(12) United States Patent
Strøm et al.

(10) Patent No.: US 11,072,588 B2
(45) Date of Patent: Jul. 27, 2021

(54) BARBITURIC ACID DERIVATIVES COMPRISING CATIONIC AND LIPOPHILIC GROUPS

(71) Applicant: UNIVERSITETET I TROMSØ—NORGES ARKTISKE UNIVERSITET, Tromsø (NO)

(72) Inventors: Morten Bøhmer Strøm, Tromsø (NO); Annette Bayer, Tromsø (NO); Stig Olov Magnus Engqvist, Tromso (NO); Marianne Hagensen Paulsen, Tromsø (NO); Dominik Ausbacher, Tromsø (NO)

(73) Assignee: Universitetet i Tromsø—Norges Arktiske Universitet, Tromsø (NO)

( * ) Notice: Subject to any disclaimer, the term of this patent is extended or adjusted under 35 U.S.C. 154(b) by 0 days.

(21) Appl. No.: 16/495,452

(22) PCT Filed: Mar. 28, 2018

(86) PCT No.: PCT/EP2018/058011
§ 371 (c)(1),
(2) Date: Sep. 19, 2019

(87) PCT Pub. No.: WO2018/178198
PCT Pub. Date: Oct. 4, 2018

(65) Prior Publication Data
US 2020/0024240 A1 Jan. 23, 2020

(30) Foreign Application Priority Data
Mar. 31, 2017 (GB) .................................... 1705255

(51) Int. Cl.
*C07D 239/62* (2006.01)
*A61P 31/04* (2006.01)
(52) U.S. Cl.
CPC ............ *C07D 239/62* (2013.01); *A61P 31/04* (2018.01)
(58) Field of Classification Search
CPC ........................... C07D 239/62; A61P 31/04
USPC ..................................................... 514/270
See application file for complete search history.

(56) References Cited

U.S. PATENT DOCUMENTS

| 4,073,927 A | 2/1978 | Freilich |
| 2003/0187005 A1 | 10/2003 | Gutman et al. |

FOREIGN PATENT DOCUMENTS

| FR | 2424262 | * 11/1979 |
| WO | 2001/012611 A1 | 2/2001 |
| WO | 2010/129665 A2 | 11/2010 |
| WO | 2011/051692 A1 | 5/2011 |

OTHER PUBLICATIONS

Bonati et al., Journal of Organometallic Chemistry, (1986), 317 (I), 121-135.*
Tadesse et al., "The Antibacterial ent-Eusynstyelamide B and Eusynstyelamides D, E, and F from the Arctic Bryozoan Tegella cf. spitzbergensis", J. Nat. Prod. 2011, 74, 837-841.
Goldhahn, H., "Basic Barbituric Acids and Barbituric Bases", Acta Chimica Academiae Scientiarum Hungarica, Budapest, HU,vol. 18, 1959, pp. 395-406.
Casagrande, C., et al., "Synthesis and antiarrhythmic activity of 5,5-disubstituted-3aminoalkylhydantoins and some heterocyclic and noncyclic analogues", Farmaco, Edizione Scientifica, Societa Chimica Italiana, Pavia, IT, vol. 29, No. 10, 1974, pp. 757-785.

* cited by examiner

*Primary Examiner* — Tracy Vivlemore
*Assistant Examiner* — Ebenezer O Sackey
(74) *Attorney, Agent, or Firm* — Fox Rothschild LLP

(57) ABSTRACT

The present invention relates to bioactive cyclic compounds and their use as antimicrobial agents. In particular, the present invention relates to barbiturate mimics of Eusynstyelamides or small antimicrobial peptides. The compounds of the invention are represented by Formula (I).

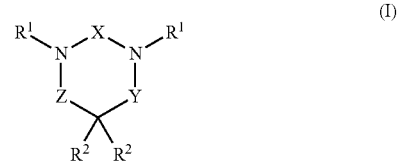

28 Claims, 4 Drawing Sheets

7(i) (4-tBu)

7(ii) (3,5-di-Br)

7(iii) (3,5-di-tBu)

7(iv) (2-Nal)

7(v) (4-F-1-Nal)

7(vi) (3,5-di-CF₃)

BARBITURIC ACID DERIVATIVES COMPRISING CATIONIC AND LIPOPHILIC GROUPS

The present invention relates to bioactive cyclic compounds and their use as antimicrobial agents, for example against Gram-positive and Gram-negative bacteria, including multi-resistant isolates.

Infections caused by multi-resistant bacteria have become a major concern to society over the past 20-25 years. There is an urgent need for the development of new antimicrobial agents to meet the worldwide emergence and spread of resistant bacteria. Resistant bacteria are currently causing the deaths of 25 000 European patients annually, and the worst scenarios estimate 10 million deaths by 2050 per year if no significant new drugs are developed.

A promising class of antimicrobial agents are cationic antimicrobial peptides (AMP's), also known as host defence peptides. AMP's are amphipathic and have a unique mode of action by targeting the inner and/or outer membranes of bacteria in a non-receptor specific manner. These molecules interact directly with the lipid bi-layer of cellular membranes.

The pharmacophore model of small AMPs has recently been applied to the design of $\beta^{2,2}$-amino acid derivatives and peptides containing them. WO 2011/051692 discloses peptide, peptidomimetic and amino acid derivatives which incorporate $\beta^{2,2}$-amino acids for use as cytolytic therapeutic agents. These compounds have a broad spectrum of antibacterial activity, for example activity against both Gram-positive and Gram-negative species. However, there is still a need for compounds having improved activity against Gram-positive and Gram-negative species.

The eusynstyelamides are a class of antimicrobials isolated from the marine Arctic bryozoan *Tegella* cf. *spitzbergensis* and the Australian ascidian *Eusynstyela latericius*, which display moderate antimicrobial activity. The antimicrobial activity of Eusynstyelamides is reported in Tadesse et al., J. Nat. Prod. 2011, 74, 837-841.

Figure 1:
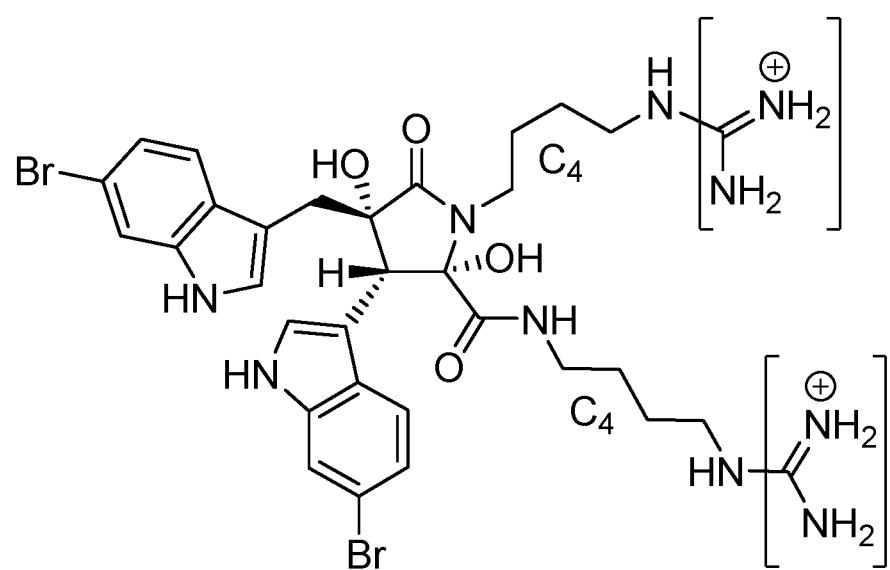

The eusynstyelamides consist of two cationic groups (amine or guanidine) and two lipophilic groups attached to a five-membered dihydroxybutyrolactam ring (see FIG. 1). This amphipathic structural arrangement of cationic and lipophilic groups in eusynstyelamides satisfies the pharmacophore model of small antimicrobial peptides (AMPs).

However, a problem with the eusynstyelamides (aside from generally only modest cytotoxic activity) is that the structure of the dihydroxybutyrolactam ring is very complex, with three stereocentres, and their synthesis is therefore complicated.

There therefore remains a need to develop antibiotic compounds exhibiting good activity, particularly against drug-resistant or otherwise problematic strains.

The present inventors have found that certain barbiturates which could be considered mimics of Eusynstyelamides or small AMPs have good anti-bacterial activity. These compounds contain two lipophilic groups geminally attached to a central scaffold that is further linked to two cationic groups.

Thus, the present invention provides a compound of Formula (I)

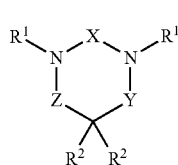

Formula (I)

or a stereoisomer, a tautomer, or a solvate thereof, wherein:
X is $CH_2$ or C=W;
Y is $CH_2$ or C=W;
Z is a bond, $CH_2$ or C=W;
W is N, O or S;
each $R^1$, which may be the same or different, comprises at least one cationic group which has a net charge of at least +1 at pH 7;
each $R^2$, which may be the same or different, is lipophilic and comprises at least 7 non-hydrogen and non-fluorine atoms;
alternatively the $R^2$ groups are linked or fused to form a lipophilic group having a total of at least 14 non-hydrogen and non-fluorine atoms, or at least 12 non-hydrogen and non-fluorine atoms when cyclic groups within each group are fused together;
at least one $R^2$ group contains a cyclic group; and
the compound has a net positive charge of at least +2 at pH 7.

The compounds of Formula (I) contain two lipophilic groups geminally attached to a central cyclic scaffold that is further linked to two cationic groups. The central scaffold ensures a rigid amphipathic structure with a specific orientation of the geminally-substituted lipophilic groups with respect to the cationic groups. Both lipophilic groups are attached to the same carbon and may be orientated above and below the plane of the central ring.

The present invention provides compounds of Formula (I) where X is $CH_2$ or C=W; Y is $CH_2$ or C=W; and Z is a bond, $CH_2$ or C=W.

Preferably at least one of X, Y and Z is C=W. For example, X may C=W, Y may be $CH_2$ and Z may be a bond or $CH_2$. More preferably, at least two of X, Y and Z are C=W. For example, X and Y may be C=W and Z may be a bond, $CH_2$ or C=W. Alternatively, Y and Z may be C=W and X may be $CH_2$. Preferably, X and Y are both C=W and Z is a bond or C=W. Most preferably, all of X, Y and Z are C=W, in particular C=O.

Preferred cyclic scaffolds for the compounds of the invention (of Formula I) are barbiturate or hydantoin, as shown below.

Thus, preferred compounds of the invention are compounds of Formula (II)

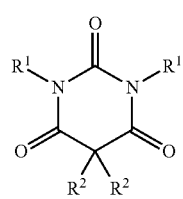

Formula (II)

wherein $R^1$ and $R^2$ are as defined herein.

Further preferred compounds of the invention are compounds of Formula (III)

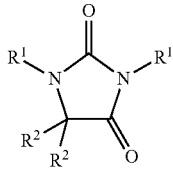

Formula (III)

wherein $R^1$ and $R^2$ are as defined herein.

W may be nitrogen, oxygen or sulfur. Preferably, W is oxygen or sulfur. More preferably, W is oxygen.

Each $R^1$ group comprises at least one cationic group which has a net charge of at least +1 at pH 7. Preferably, the net charge of each $R^1$ group is +1 at pH 7.

Whilst each $R^1$ group may be different, preferably each $R^1$ group is the same.

Preferably, each $R^1$ group comprises 2-15 non-hydrogen atoms. More preferably, each $R^1$ group comprises 3-12 non-hydrogen atoms. Most preferably, each $R^1$ group comprises 5-8 non-hydrogen atoms.

The cationic group may typically be a cationic amine group or a cationic imine (iminium) group.

Thus, the cationic group may preferably comprise at least one of $-NR_3^+$, $=NR_2^+$, $-NR_2^+-$, and $=NR^+-$, wherein each R is the same or different at each occurrence and is H or alkyl.

Example of groups comprising an $=NR_2^+$ group are the groups $-NR-C(=NR_2^+)-NR_2$ or $-N(-C(=NR_2^+)-NR_2)-$.

Examples of groups comprising an $-NR_2^+-$ group are 4-6 membered saturated rings such as cationic piperidine, piperazine, morpholine, triazine, pyrrolidone, imidazolidine or pyrazolidine.

Examples of groups comprising an $=NR^+-$ group are 4-6 membered unsaturated rings such as cationic diazine, oxazine, thiazine, pyridine, pentazole, tetrazole, triazole, furazan, oxadiazole, thiadiazole, dithiazole, thiazole, isothiazole, pyrazole, imidazole, oxazole, isoxazole or pyrrole.

Preferably, the cationic group comprises $-NR_3^+$, or $=NR_2^+$, wherein each R is the same or different at each occurrence and is H or alkyl. More preferably, the cationic group comprises $-NR_3^+$ or $-NR-C(=NR_2^+)-NR_2$, wherein each R is the same or different at each occurrence and is H or alkyl.

Preferably, R is H or $C_{1-6}$ alkyl, more preferably H, $CH_3$ or $CH_2CH_3$. Most preferably, R is H or $CH_3$.

The cationic group may preferably be a cationic amine group or a cationic guanidine group, or an isostere or bioisostere thereof. More preferably, the cationic group is a cationic amine group or a cationic guanidine group.

Each $R^1$ group can be defined as $-M-R_y$, wherein:
M is a bond, alkyl, alkenyl, alkynyl, heteroalkyl, alkoxy, haloalkoxy, aryl, heteroaryl, cycloalkyl, or heterocloalkyl, each of which may optionally be substituted; and
$R_y$ comprises a cationic group, such as those listed above.

Preferably, M is alkyl, alkenyl, alkynyl, heteroalkyl, alkoxy or haloalkoxy. More preferably, M is alkyl, alkenyl or alkynyl, most preferably alkyl. For example, M may be $C_{2-8}$ alkyl, $C_{2-8}$ alkenyl or $C_{2-8}$ alkynyl. Most preferably, M is $C_{3-5}$ alkyl, $C_{3-5}$ alkenyl or $C_{3-5}$ alkynyl, in particular $C_{3-5}$ alkyl.

Thus, preferably each $R^1$ group is

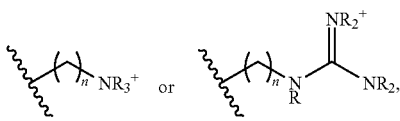

preferably,

wherein
R is H or alkyl, preferably H, $CH_3$ or $CH_2CH_3$, more preferably H; and
n is 1-10, preferably 2-8, more preferably 3-5.
Preferably, R is H, $CH_3$ or $CH_2CH_3$ and n is 2-8.
More preferably, R is H and n is 3-5.
Thus, even more preferably, $R^1$ is

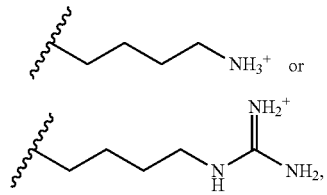

most preferably

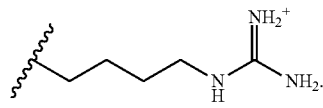 [SMILES: *CCCCNC(N)=[NH2+]]

Each $R^2$ group is lipophilic and comprises at least 7 non-hydrogen and non-fluorine atoms. It is also essential that at least one $R^2$ group contains a cyclic group.

Each lipophilic $R^2$ group may contain the heteroatoms O, N or S but typically there is no more than one of the heteroatoms O, N and S, and preferably it is nitrogen. Each $R^2$ group will preferably have no more than 2 polar groups (e.g. $-Br$, $-I$ or $-CF_3$).

The $R^2$ groups, which are geminally attached to the central scaffold, may be linked or fused to form a lipophilic group having a total of at least 14 non-hydrogen and non-fluorine atoms. When one or more cyclic groups from one $R^2$ group is fused with one or more cyclic groups from the other $R^2$ group, the combined total number of non-hydrogen and non-fluorine atoms for the two $R^2$ groups is at least 12. Examples of linked or fused $R_2$ groups include those shown in the structures below:

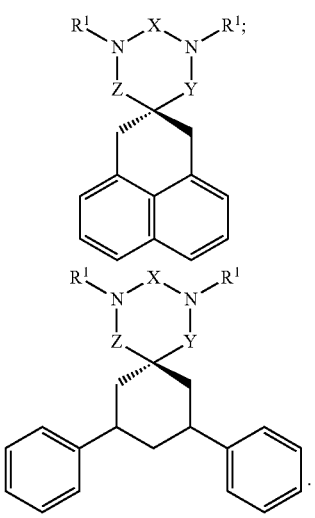

Preferably however, the R² groups are not linked or fused.

There is no maximum number of non-hydrogen and non-fluorine atoms that may be present in the R² groups. However, if the R² groups are too large the compounds can become toxic to human red blood cells. Thus, each of the R² groups may have a maximum number of non-hydrogen and non-fluorine atoms of 20, preferably 18, and more preferably 15.

Preferably, each R² group comprises at least 8 non-hydrogen and non-fluorine atoms. More preferably, each R² group comprises at least 9 non-hydrogen and non-fluorine atoms. If one R² group contains 7 non-hydrogen and non-fluorine atoms then the other R² group preferably contains at least 8, preferably at least 9 non-hydrogen and non-fluorine atoms.

Thus, each R² group may preferably comprise 8-20 or 8-15 non-hydrogen and non-fluorine atoms, more preferably 9-20 or 9-15 non-hydrogen and non-fluorine atoms.

Each R² group may be selected from alkyl, alkenyl, alkynyl, heteroalkyl, alkoxy, haloalkoxy, aryl, heteroaryl, cycloalkyl, or heterocycloalkyl, each of which may optionally be substituted. Preferably, R² comprises an optionally substituted aryl or heteroaryl group. For example, R² may comprise optionally substituted phenyl, naphthyl and pyridine, preferably optionally substituted phenyl or naphthyl.

The optional substituents are preferably selected from the group consisting of:
halo, —CN, —R⁴NO₂, —R⁴OR³, —R⁴(=O)R³, —R⁴OC(=O)R³, —R⁴O₂R³, —R⁴N(R³)₂, —R⁴(=O)N(R³)₂, —R⁴OC(=O)N(R³)₂, —R⁴NR³(=O)R³, —R⁴NR³(=O)OR³, alkyl, alkenyl, alkynyl, haloalkyl, alkoxy, haloalkoxy, aryl, heteroaryl, cycloalkyl, and heterocycloalkyl;
wherein
R⁴ is a bond or alkyl, preferably a bond or $C_{1-6}$ alkyl, more preferably a bond; and
R³ is H, alkyl, alkenyl, alkynyl, heteroalkyl, alkoxy, haloalkoxy, aryl, heteroaryl, cycloalkyl, or heterocycloalkyl, preferably H or $C_{1-6}$ alkyl, more preferably H.

More preferred substituents are halo, $C_{1-6}$ alkyl, $C_{1-6}$ alkoxy, $C_{1-6}$ haloalkyl, $C_{1-6}$ haloalkoxy, $C_{6-10}$ aryl, $C_{4-6}$ heteroaryl, $C_{3-6}$ cycloalkyl, or $C_{3-6}$ heterocycloalkyl.

Particularly preferred substituents include halo, $C_{1-4}$ alkyl, $C_{1-4}$ alkoxy, $C_{1-4}$ haloalkyl, $C_{1-4}$ haloalkoxy, phenyl and naphthyl.

Most preferably, the substituents are selected from halo, t-butyl, and —CF₃. Most preferred halo substituents are I and Br.

Preferably, both R² groups contain a cyclic group. In this case, each R² group can be defined as -L-$R_x$, wherein:
L is a bond, alkyl, alkenyl, alkynyl, heteroalkyl, alkoxy or haloalkoxy; and
$R_x$ is aryl, heteroaryl, cycloalkyl, or heterocycloalkyl group, optionally substituted by any of the substituents listed above.

Preferably, L is $C_{1-3}$ alkyl. More preferably, L is —CH₂—.

Each $R_x$ group may comprise two or more cyclic groups, which may be connected or fused, preferably fused. For example, each $R_x$ group may comprise an optionally substituted naphthalene ring.

Preferably, $R_x$ is an optionally substituted aryl or heteroaryl group. For example, $R_x$ may be selected from optionally substituted phenyl, naphthyl and pyridine, preferably optionally substituted phenyl or naphthyl.

Preferably, L is —CH₂— and $R_x$ is phenyl or naphthyl optionally substituted with halo, t-butyl, or —CF₃.

Preferred R² groups are shown in the Examples.

Both R² groups are preferably the same, if only for ease of synthesis. However it may be desirable for one R² group to incorporate a cyclic group, as discussed above, e.g. represented by -L-$R_x$, and for the other R² group to be alkyl, alkenyl, alkynyl, or heteroalkyl. These groups are optionally branched or substituted (as discussed above) but preferably are linear and unsubstituted.

The term "alkyl" refers to straight and branched saturated aliphatic hydrocarbon chains. Preferably, alkyl refers to $C_{1-10}$ alkyl. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" refers to straight and branched hydrocarbon chains configuration having one or more, preferably one or two, carbon-carbon double bonds. Preferably, alkenyl refers to $C_{2-10}$ alkenyl. Examples of alkenyl groups include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

The term "alkynyl" refers to straight and branched hydrocarbon chains having one or more, preferably one or two, carbon-carbon triple bonds. Preferably, alkynyl refers to $C_{2-10}$ alkynyl. Examples of alkynyl groups include, but are not limited to, ethynyl, propynyl, and propargyl.

The term "alkoxy" refers to an —O-alkyl group. Preferably, alkoxy refers to $C_{1-10}$ alkoxy. Example alkoxy groups include, but are not limited to, methoxy, ethoxy, propoxy (e.g., n-propoxy and isopropoxy), and t-butoxy.

The term "haloalkyl" refers to straight and branched saturated aliphatic hydrocarbon chains substituted with 1 or more halogens (fluoro (F), chloro (Cl), bromo (Br), and iodo (I)). Preferably, haloalkyl refers to $C_{1-10}$ haloalkyl. Examples of haloalkyl groups include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl.

The term "haloalkoxy" refers to a haloalkyl group as defined above attached through an oxygen bridge. Preferably, haloalkoxy refers to $C_{1-10}$ haloalkoxy. Examples of haloalkoxy groups include, but are not limited to, trifluoromethoxy, 2,2,2-trifluoroethoxy, and pentafluorothoxy.

The term "cycloalkyl" refers to cyclized alkyl groups, including mono-, bi-or poly-cyclic ring systems. Preferably, cycloalkyl refers to $C_{3-10}$ cycloalkyl, more preferably $C_{3-6}$ cycloalkyl. Example cycloalkyl groups include, but are not limited to, cyclopropyl, cyclobutyl, cyclopentyl, cyclohexyl, and norbornyl.

The term "aryl" refers to monocyclic or polycyclic aromatic hydrocarbons, including, for example, phenyl, naphthyl, and phenanthrenyl. Preferably, aryl refers to $C_{6-12}$ aryl, more preferably $C_{6-10}$ aryl.

The term "heterocycloalkyl" refers to cyclized alkyl groups, including mono-, bi-or poly-cyclic ring systems that contain carbon atoms and 1, 2, 3 or 4 heteroatoms independently selected from the group consisting of N, O and S. Preferably, heterocycloalkyl refers to $C_{3-10}$ heterocycloalkyl, more preferably $C_{3-6}$ heterocycloalkyl. Example heterocycloalkyl groups include, but are not limited to, oxirane, pyrrolidone, tetrahydrofuran, piperidine, piperazine, tetrahydropyran, and thiane.

The term "heteroaryl" refers to monocyclic and polycyclic aromatic hydrocarbons that include at least one heteroatom ring member such as sulfur, oxygen, or nitrogen. Preferably, heteroaryl refers to $C_{6-12}$ heteroaryl, more preferably $C_{6-10}$ heteroaryl. Examples of heteroaryl groups include, but are not limited to, pyridine, pyrimidine, pyrazine, pyridazine, triazine, furan, quinoline, isoquinoline, thiophene, imidazole, thiazole, indole, pyrrole, oxazole, benzofuran, benzothiophene, benzothiazole, isoxazole, pyrazole, triazole, tetrazole, indazole, 1,2,4-thiadiazole, isothiazole, purine, carbazole, benzimidazole, indoline, benzodioxolane, and benzodioxane.

As described elsewhere herein, compounds of the present invention exhibit antimicrobial activity. Without wishing to be bound by theory, it is believed that the compounds of the present invention may exert a cytotoxic effect through a direct membrane-affecting mechanism and thus may be termed membrane acting antimicrobial agents. These compounds may be lytic, destabilising or even perforating the cell membrane. This may offer a distinct therapeutic advantage over agents which act on or interact with proteinaceous components of the target cells, e.g. cell surface receptors. While mutations may result in new forms of the target proteins leading to antibiotic resistance, it is much less likely that radical changes to the lipid membranes could occur to prevent the cytotoxic effect. A lytic effect may cause very rapid cell death and thus has the advantage of killing bacteria before they have a chance to multiply. Again, without wishing to be bound by theory, it is believed that molecules of the invention may be attracted to the negatively charged phospholipids of the cell membrane by virtue of the presence of the cationic groups, and that lipophilic groups may be able to destabilise the normal three dimensional lipid bi-layer configuration of microbial (e.g. bacterial or fungal) cell membranes.

This interaction may increase permeability and result in a loss of membrane integrity and eventually cell lysis and death.

Thus, the present invention provides compounds of Formula (I) for use in destabilising and/or permeabilising microbial cell membranes. By 'destabilising' is meant a perturbation of the normal three dimensional lipid bi-layer configuration including but not limited to membrane thinning, increased membrane permeability (typically not involving channels) to water, ions or metabolites etc. which also impairs the respiratory systems of the bacteria.

The present invention also provides the compounds of Formula (I) (or compositions or formulations comprising a compound of Formula (I)) for use in therapy, in particular for use in the treatment of microbial infections (e.g. a bacterial and/or fungal infection). Thus, in one aspect, the present invention provides the compounds defined herein for use in the treatment of a bacterial infection. In another aspect, the present invention also provides the compounds defined herein for use in the treatment of a fungal infection. Treatment includes prophylactic treatment.

Preferred compounds of the invention are active both as antibacterial agents and antifungal agents.

Alternatively viewed, the present invention provides the use of compounds of Formula (I) as an antimicrobial agent (e.g. antibacterial or antifungal agent).

Alternatively viewed, the present invention provides a method of treating a microbial infection (e.g. a bacterial and/or fungal infection) which method comprises administering to a patient in need thereof a therapeutically effective amount of a compound of the invention as defined herein.

A therapeutically effective amount will be determined based on the clinical assessment and can be readily monitored. Typically, the amount administered should be effective to kill all or a proportion of the target microbes or to prevent or reduce their rate of reproduction or otherwise to lessen their harmful effect on the body. The clinician or patient should observe improvement in one or more of the parameters or symptoms associated with the infection.

Further alternatively viewed, the present invention provides the use of a compound of the invention as defined herein in the manufacture of a medicament for treating a microbial infection (e.g. a bacterial and/or fungal infection).

As mentioned above, compounds of the present invention may be used in the treatment of a bacterial infection. Such infections include infections with Gram positive (G+) bacteria or Gram negative (G−) bacteria.

For example, compounds of the present invention may be used in the treatment of an *Escherichia coli* (Ec) infection, a *Pseudomonas aeruginosa* (Pa) infection, a *Staphylococcus aureus* (Sa) infection, a *Corynebacterium glutamicum* (Cg) infection, an *Enterococcus faecium* infection, an *Acinetobacter baumannii* infection, and/or a *Klebsiella pneumoniae* infection.

Compounds of the present invention may also be used in the treatment of cystic fibrosis caused by a *Pseudomonas aeruginosa* infection.

Compounds of the present invention may also be used in the treatment of a *Chlamydophila pneumoniae* infection.

Compounds of the present invention may also be used to improve and/or assist wound healing, e.g. in immune-compromised patients.

As mentioned above, compounds of the present invention may be used in the treatment of a fungal infection. For example, compounds of the present invention may be used in the treatment of *Candida albicans* (Ca) infection, a *Rhodotorula* sp. (Rh) infection and/or an *Aureobasidium pullulans* (Ap) infection. In particular, compounds of the present invention may be used in the treatment of *Candida albicans* (Ca) infection.

Subjects treated in accordance with the present invention will preferably be humans but veterinary treatments are also contemplated.

These treatments may involve co-administration with another antimicrobial agent. Thus, in a further aspect the present invention provides a product comprising (a) a compound of Formula (I), and (b) a further antimicrobial agent, as a combined preparation for separate, simultaneous or sequential use in the treatment or prevention of an antimicrobial infection.

Such antimicrobial compounds also have non-therapeutic uses (ex vivo uses), for example in agriculture or in domestic or industrial situations as sterilising agents for materials susceptible to microbial contamination. Thus, in a further aspect, the present invention provides the use of the compounds of the invention as antimicrobial agents, particularly as antibacterial and/or antifungal agents. Methods of treating environmental or agricultural sites or products, as well as foodstuffs and sites of food production, or surfaces or tools e.g. in a hospital environment with one or more of the compounds of the invention to reduce the numbers of viable bacteria present or limit bacterial growth or reproduction constitute further aspects of the present invention.

Compounds of the present invention may also have antifouling, anti-biofilm (e.g. against bacterial or fungal biofilms) and/or antiparasitic uses. Thus, compounds of the present invention may be used as anti-fouling agents, anti-biofilm agents (e.g. against bacterial or fungal biofilms) and/or antiparasitic agents. Accordingly, the invention provides compounds as defined herein for use in treating a bacterial or fungal infection, wherein said bacterial or fungal infection is in the form of a biofilm. The invention also provides compounds as defined herein for use in treating a parasitic infection.

A biofilm is a collection, or community, of microorganisms surrounded by a matrix of extracellular polymers (also known in the art as a glycocalyx). These extracellular polymers are typically polysaccharides, notably polysaccharides produced by the organisms themselves, but they can contain other biopolymers as well. A biofilm will typically be attached to a surface, which may be inert or living, but it has also been observed that biofilms may form from microrganisms attached to each other or at any interface. Such a mode of growth is protective to the microorganisms, and renders them difficult to remove or eradicate. Biofilms cause significant commercial, industrial and medical problems, in terms of infections, contamination, fouling and spoilage etc.

Microorganisms in a biofilm environment do not display the same susceptibilities to anti-microbial agents, e.g. antibiotics, antifungals and microbicides, and host immune defences or clearance mechanisms. It is thought that this resistance is due to the barrier effect of the extracellular matrix and/or a phenotypic change in the microbes themselves. It is also believed that microorganisms in biofilms may grow more slowly, and as a result take up anti-microbial agents more slowly.

Thus, bacteria grown in biofilms are often more tolerant to antimicrobial agents than their planktonic counterparts. Susceptibility testing of planktonic bacteria may fail to predict in vivo resistance of device-related infections to antimicrobial agents.

It is therefore particularly advantageous to provide agents which are active antimicrobials and which are able to exert their effect even against microbes which exist as a biofilm. This property is demonstrated in the Examples and preferred compounds of the invention are active against biofilms and prevent biofilm formation.

Compounds of the present invention may also have anti-cancer (e.g. anti-tumour) activity. Accordingly, in some embodiments, the invention provides a compound of the present invention for use in the treatment of cancer (e.g. in the treatment of tumours such as solid tumours). Thus, compounds of the invention may be used as antitumoural agents. Alternatively viewed, the present invention provides a method of treating cancer (e.g. a tumour) which method comprises administering to a patient in need thereof a therapeutically effective amount of a compound of the invention as defined herein. Further alternatively viewed, the present invention provides the use of compound of the invention as defined herein in the manufacture of a medicament for treating cancer (e.g. a tumour). This property is demonstrated in the Examples and preferred compounds of the invention are active against tumours.

Formulations comprising one or more compounds of the invention in admixture with a suitable diluent, carrier or excipient constitute a further aspect of the present invention. Such formulations may be for, inter alia, pharmaceutical (including veterinary) purposes. Suitable diluents, excipients and carriers are known to the skilled man.

The compositions (formulations), e.g. pharmaceutical compositions, according to the invention may be presented, for example, in a form suitable for oral, nasal, parenteral, intravenal, topical or rectal administration. As used herein, the term "pharmaceutical" includes veterinary applications of the invention.

The active compounds defined herein may be presented in the conventional pharmacological forms of administration, such as tablets, coated tablets, nasal sprays, solutions, emulsions, liposomes, powders, capsules or sustained release forms.

Formulations for topical administration are preferably in the form of a gel, cream, lotion, paste or other preparation which is more viscous than water. Further formulations for topical application include dressings, gauzes etc. which have been impregnated with a compound of the invention; when impregnating such materials the preparation containing a compound of the invention need not be more viscous than water. Conventional pharmaceutical excipients as well as the usual methods of production may be employed for the preparation of these forms.

Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the active compounds preferably contain 0.1-10 mg, for example 1-5 mg of the antimicrobial agent. The pharmaceutical compositions may additionally comprise further active ingredients, including other cytotoxic agents such as other antimicrobial compounds. Other active ingredients may include different types of antibiotics.

The bioactive compounds, when used in topical compositions, are generally present in an amount of at least 0.1%, by weight. In most cases, it is not necessary to employ the compound of the invention in an amount greater than 1.0%, by weight.

In employing such compositions systemically (intra-muscular, intravenous, intraperitoneal), the active compound may be present in an amount to achieve a serum level of the bioactive molecule of at least about 5 μg/ml. In general, the serum level need not exceed 500 μg/ml. A preferred serum level is about 100 ug/ml. Such serum levels may be achieved by incorporating the bioactive compound in a composition to be administered systemically at a dose of from 1 to about 10 mg/kg. In general, the compound(s) need not be administered at a dose exceeding 100 mg/kg.

As described elsewhere herein, molecules of the invention have antimicrobial activity.

The invention will now be described by way of the following non-limiting Examples with reference to the Figures in which:

FIG. 1—shows the general structure of the Eusynstyelamides

Figure 2:
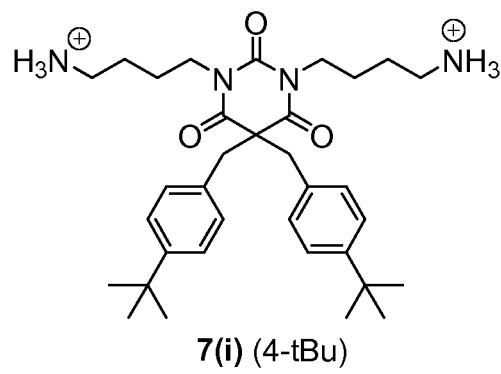
Figure 2:
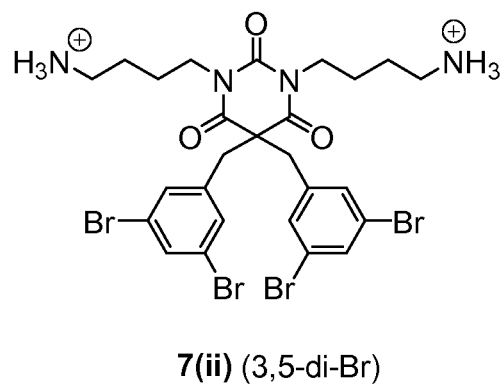
Figure 2:
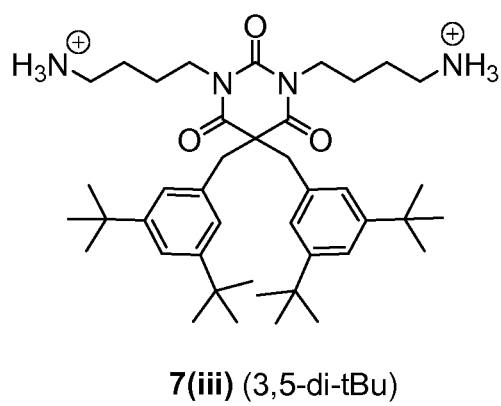
Figure 2:
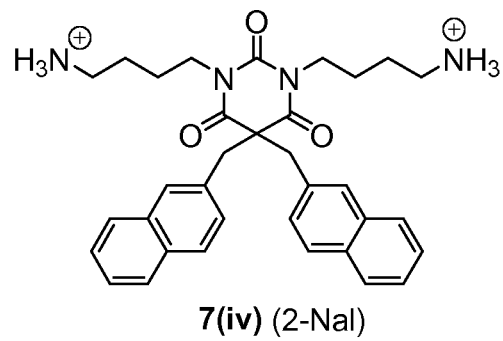
Figure 2:
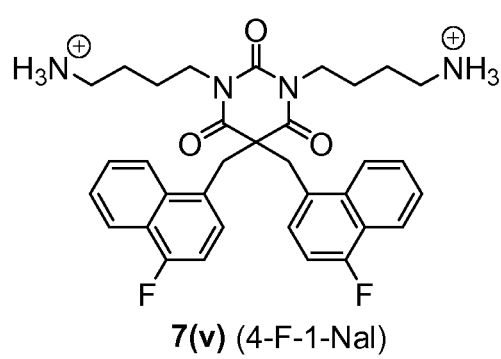
Figure 2:
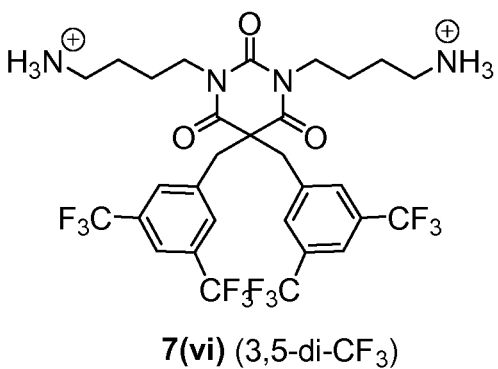

FIG. 2—shows the structures of amphipathic barbiturates of Formula (I). For each compound the counter-ion is $CF_3OO^-$.

Figure 3:
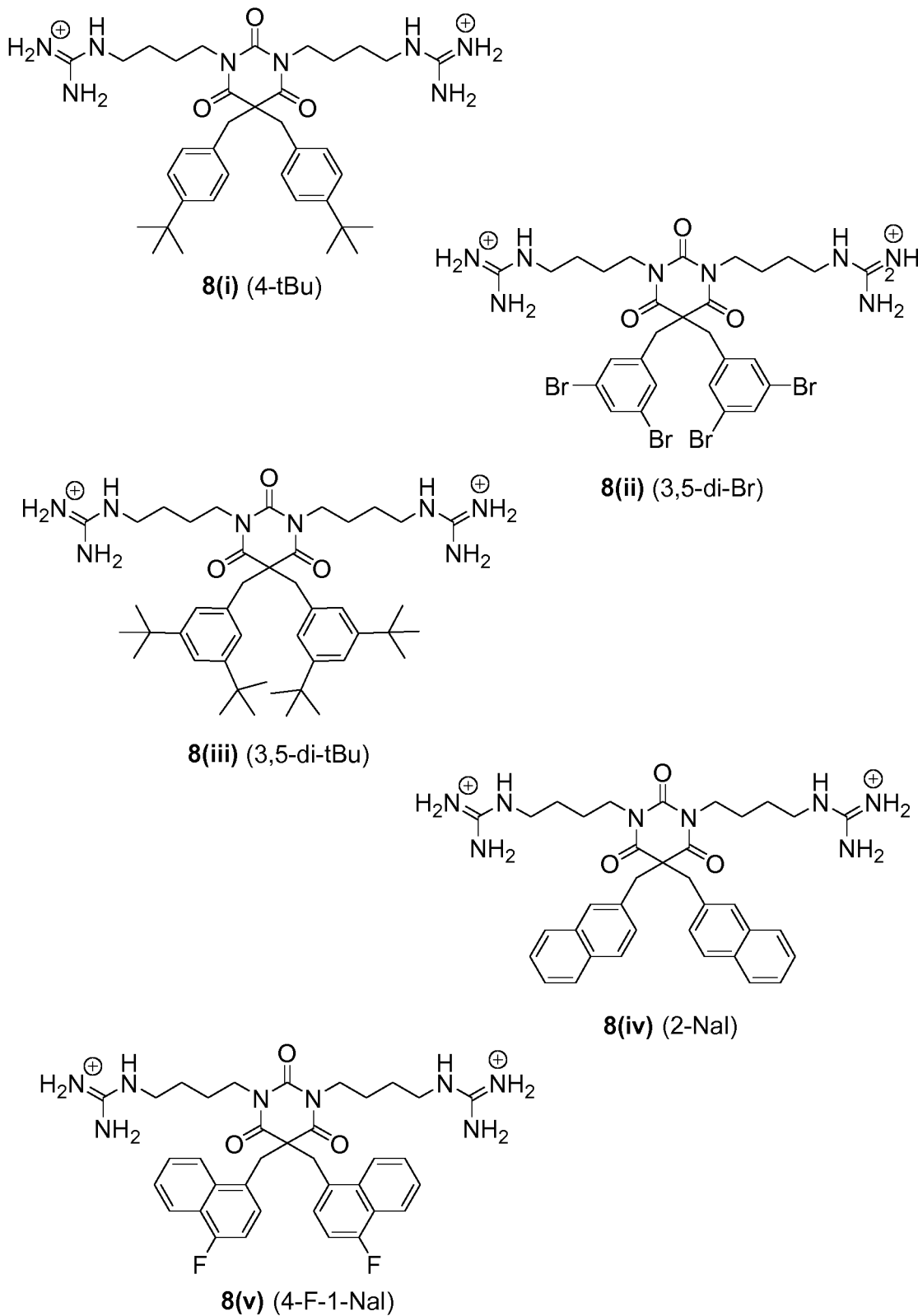

FIG. 3—shows the structures of amphipathic barbiturates of Formula (I). For each compound the counter-ion is $CF_3OO^-$.

Figure 4:
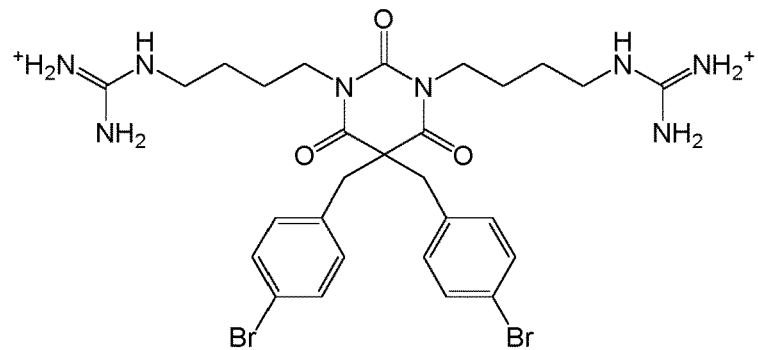
Figure 4:
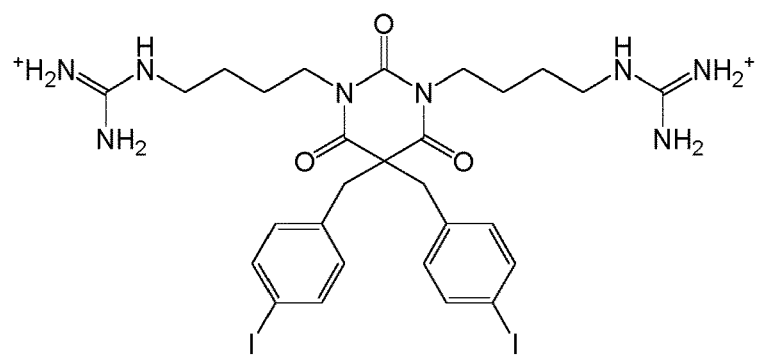
Figure 4:
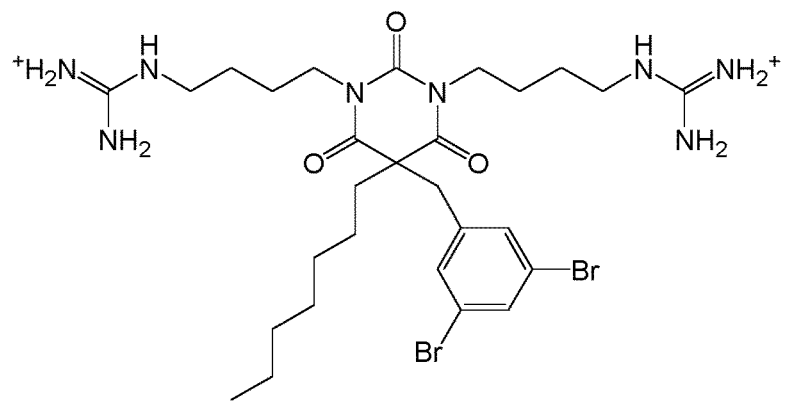
Figure 4:
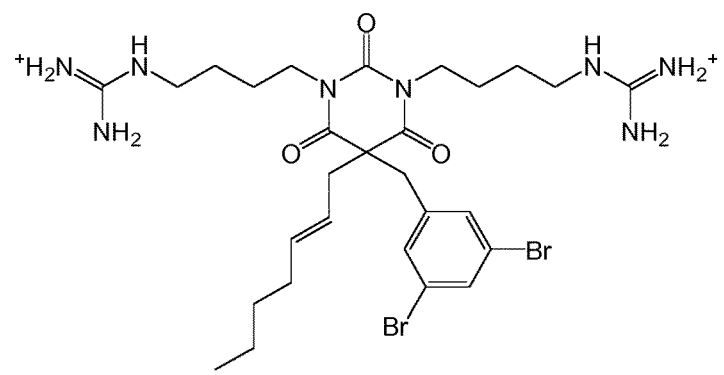

FIG. 4—shows further compounds of interest of Formula (I).

EXAMPLES

Example 1

Antimicrobial Activity Against Bacterial Reference Strains

Two series of amphipathic barbiturates were prepared by the methods set out below.

Series 7 consisted of barbiturates with two cationic amino groups and series 8 encompassed barbiturates with two cationic guanidine groups (FIGS. 2 and 3). The barbiturates were initially screened for antimicrobial activity against antibiotic susceptible Gram-positive and Gram-negative reference strains. The results are shown below in Table 1.

TABLE 1

Antimicrobial activity (MIC in μg/mL) against antibiotic susceptible Gram- positive and Gram-negative reference strains.

| Compound | $Mw^b$ | Antimicrobial activity$^a$ | | | |
|---|---|---|---|---|---|
| | | S. a | C. g | E. c | P. a |
| 7(i) | 790.83 | 4 | 1 | 4 | 8 |
| 7(ii) | 994.20 | 4 | 1 | 4 | 8 |
| 7(iii) | 903.04 | 1 | 0.25 | 2 | 4 |
| 7(iv) | 778.74 | 8 | 1 | 16 | 16 |
| 7(v) | 814.72 | 4 | 1 | 16 | 8 |

TABLE 1-continued

Antimicrobial activity (MIC in μg/mL) against antibiotic susceptible Gram- positive and Gram-negative reference strains.

| Compound | $Mw^b$ | Antimicrobial activity$^a$ | | | |
|---|---|---|---|---|---|
| | | S. a | C. g | E. c | P. a |
| 7(vi) | 950.61 | 8 | 1 | 8 | 8 |
| 8(i) | 874.91 | 1 | <0.13 | 2 | 4 |
| 8(ii) | 1078.28 | 1 | 0.25 | 2 | 4 |
| 8(iii) | 987.12 | 1 | 0.25 | 4 | 4 |
| 8(iv) | 862.82 | 1 | 0.25 | 1 | 8 |
| 8(v) | 898.77 | 1 | 0.25 | 1 | 4 |
| Oxytetracycline | 460.434 | 0.65 | 0.65 | 2.5 | 20 |

$^a$Bacterial reference strains:
S. a   Staphylococcus aureus ATCC 9144,
C. g   Corynebacterium glutamicum ATCC 13032,
E. c   Escherichia coli ATCC 25922, and
P. a   Pseudomonas aeruginosa PA01, DSM 19880 (ATCC 15692).
$^b$Molecular weight including 2 equiv. of $CF_3OO^-$, i.e. + Mw 228.05.

For the amine barbiturates of series 7 the minimum inhibitory concentration (MIC) values ranged from 0.25-8 μg/mL against the Gram-positive strains S. aureus and C. glutamicum, and MIC values from 2-16 μg/mL against the Gram-negative bacteria E. coli and P. aeruginosa.

Higher antimicrobial activity was therefore in general observed against the Gram-positive bacteria than against the Gram-negative bacteria, although the differences were marginal for the most potent amine barbiturates of series 7.

The most potent amine barbiturate was 7(iii), which had two super-bulky lipophilic 3,5-di-tBu-benzylic side-chains and displayed MIC values in the very lower range of 0.25-4 μg/mL against all the reference strains.

The two barbiturates 7(i) and 7(ii) were the second most potent derivatives displaying MIC values of 1-8 μg/mL against the reference strains. These had smaller lipophilic side-chains, and revealed a correlation between side-chain size and antimicrobial activity.

Guanylation of the amine barbiturates of series 7 resulted in a striking increase in antimicrobial activity for the resulting guanidine barbiturates of series 8. The highly potent guanylated barbiturates of series 8 showed a narrow range in MIC values of <0.13-1 μg/mL against the Gram-positive strains S. aureus and C. glutamicum, and MIC 1-8 μg/mL against the Gram-negative bacteria E. coli and P. aeruginosa.

The guanylated barbiturates thereby showed high potency against the Gram-positive reference strains and were considered equipotent. Antimicrobial activity against the Gram-negative reference strains revealed 8(i), 8(ii), and 8(v) as the most potent derivatives with MIC values 1-4 μg/mL against E. coli and P. aeruginosa.

The guanidine analogue 8(iii) (MIC: 4 μg/mL) followed thereafter and was an analogue of the highly potent and super bulky amine barbiturate 7(iii).

Antimicrobial Activity Against 30 Multi-Resistant Clinical Isolates

The barbiturates were also screened against a panel of 30 multi-resistant clinical isolates of Gram-positive and Gram-negative bacteria, including isolates with extended spectrum β-lactamase-carbapenemase (ESBL-CARBA) production and colistin resistance.

The antimicrobial activity (MIC in μg/ml) for the compounds tested is shown in Table 2 below. Toxicity is displayed as haemolytic activity against human RBCs ($EC_{50}$ in μg/ml) and a selectivity index in parenthesis ($EC_{50}$/MIC values) against individual isolates.

TABLE 2

| | Compound | | | | | |
|---|---|---|---|---|---|---|
| | 7(i) | 7(ii) | 7(iii) | 7(iv) | 7(v) | 7(vi) |
| | | | RBC | | | |
| | 143 | 83 | <4 | 243 | 160 | 183 |
| Clinical isolates | | | Antimicrobial activity | | | |
| S. aureus N315 | 8 (18) | 4 (21) | 2 (<2) | 8 (30) | 8 (20) | 16 (11) |
| S. aureus NCTC 10442 | 8 (18) | 4 (21) | 2 (<2) | 8 (30) | 8 (20) | 16 (11) |
| S. aureus strain 85/2082 | 8 (18) | 4 (21) | 2 (<2) | 8 (30) | 4 (40) | 16 (11) |
| S. aureus strain WIS | 8 (18) | 4 (21) | 2 (<2) | 8 (30) | 8 (20) | 16 (11) |
| S. aureus IHT 99040 | 8 (18) | 4 (21) | 2 (<2) | 8 (30) | 8 (20) | 16 (11) |
| E. faecium 50673722 | 8 (18) | 4 (21) | 2 (<2) | 16 (15) | 8 (20) | 8 (23) |
| E. faecium 50901530 | 4 (36) | 4 (21) | 2 (<2) | 8 (30) | 4 (40) | 8 (23) |
| E. faecium K36-18 | 8 (18) | 8 (10) | 2 (<2) | 16 (15) | 8 (20) | 16 (11) |
| E. faecium 50758899 | 8 (18) | 4 (21) | 2 (<2) | 16 (15) | 8 (20) | 16 (11) |
| E. faecium TUH50-22 | 8 (18) | | 2 (<2) | 8 (30) | 4 (40) | 8 (23) |
| E. coli 50579417 | 8 (18) | 8 (10) | 4 (<1) | 16 (15) | 16 (10) | 16 (11) |
| E. coli 50639799 | 8 (18) | 8 (10) | 4 (<1) | 16 (15) | 16 (10) | 16 (11) |
| E. coli 50676002 | 4 (36) | 8 (10) | 8 (<0.5) | 16 (15) | 16 (10) | 16 (11) |
| E. coli 50739822 | 8 (18) | 8 (10) | 4 (<1) | 16 (15) | 16 (10) | 16 (11) |
| E. coli 50857972 | 4 (36) | 8 (10) | 4 (<1) | 16 (15) | 16 (10) | 8 (23) |
| P. aeruginosa K34-7 | >32 (—) | 16 (5) | 8 (<0.5) | 32 (8) | 32 (5) | 32 (6) |
| P. aeruginosa K34-73 | >32 (—) | 16 (5) | 16 (<2.5) | 32 (8) | 32 (5) | 32 (6) |
| P. aeruginosa K44-24 | >32 (—) | 16 (5) | 8 (<0.5) | >32 (—) | 32 (5) | 32 (6) |
| P. aeruginosa 50692172 | >32 (—) | 16 (5) | 8 (<0.5) | 32 (8) | 16 (10) | 32 (6) |
| P. aeruginosa 50692520 | >32 (—) | 16 (5) | 8 (<0.5) | 32 (8) | 16 (10) | 32 (6) |
| K. pneumoniae K47-25* | >32 (—) | 16 (5) | 16 (<2.5) | >32 (—) | >32 (—) | >32 (—) |
| K. pneumoniae K66-45 | 32 (4) | 16 (5) | 8 (<0.5) | >32 (—) | 32 (5) | 32 (6) |
| K. pneumoniae 50531633* | 16 (9) | 8 (10) | 8 (<0.5) | 32 (8) | 16 (10) | 32 (6) |
| K. pneumoniae 50625602 | 16 (9) | | 8 (<0.5) | >32 (—) | 32 (5) | 32 (6) |
| K. pneumoniae 50667959 | 32 (4) | 16 (5) | 8 (<0.5) | >32 (—) | 32 (5) | 32 (6) |
| A. baumanii K12-21 | 16 (9) | 16 (5) | 4 (<1) | 32 (8) | 32 (5) | 16 (11) |
| A. baumanii K44-35 | 32 (4) | 16 (5) | 4 (<1) | 32 (8) | 32 (5) | 32 (6) |
| A. baumanii K47-42 | 16 (9) | 16 (5) | 4 (<1) | 32 (8) | 32 (5) | 32 (6) |
| A. baumanii K55-13 | 16 (9) | 16 (5) | 4 (<1) | 32 (8) | 32 (5) | 32 (6) |
| A. baumanii K63-58* | 16 (9) | 16 (5) | 4 (<1) | 16 (15) | 16 (10) | 32 (6) |

| | Compound | | | | |
|---|---|---|---|---|---|
| | 8(i) | 8(ii) | 8(iii) | 8(iv) | 8(v) |
| | | | RBC | | |
| | 77 | 56 | <4 | 133 | 88 |
| Clinical isolates | | | Antimicrobial activity | | |
| S. aureus N315 | 2 (39) | 2 (28) | 4 (<1) | 8 (17) | 2 (44) |
| S. aureus NCTC 10442 | 2 (39) | 2 (28) | 2 (<2) | 8 (17) | 2 (44) |
| S. aureus strain 85/2082 | 2 (39) | 2 (28) | 2 (<2) | 8 (17) | 2 (44) |
| S. aureus strain WIS | 2 (39) | 2 (28) | 2 (<2) | 8 (17) | 2 (44) |
| S. aureus IHT 99040 | 2 (39) | 2 (28) | 2 (<2) | 8 (17) | 2 (44) |
| E. faecium 50673722 | 2 (39) | 4 (14) | 2 (<2) | 16 (8) | 4 (22) |
| E. faecium 50901530 | 4 (19) | 2 (28) | 2 (<2) | 8 (17) | 4 (22) |
| E. faecium K36-18 | 2 (39) | 4 (14) | 2 (<2) | 16 (8) | 4 (22) |
| E. faecium 50758899 | 2 (39) | 4 (14) | 2 (<2) | 16 (8) | 4 (22) |
| E. faecium TUH50-22 | 2 (39) | 2 (28) | 2 (<2) | 8 (17) | 4 (22) |
| E. coli 50579417 | 4 (19) | 4 (14) | 16 (<0.25) | 16 (8) | 8 (11) |
| E. coli 50639799 | 4 (19) | 4 (14) | 8 (<0.5) | 8 (17) | 4 (22) |
| E. coli 50676002 | 4 (19) | 4 (14) | 16 (<0.25) | 8 (17) | 4 (22) |
| E. coli 50739822 | 4 (19) | 4 (14) | 8 (<0.5) | 8 (17) | 8 (11) |
| E. coli 50857972 | 4 (19) | 4 (14) | 8 (<0.5) | 8 (17) | 4 (22) |
| P. aeruginosa K34-7 | 16 (5) | 8 (7) | 16 (<0.25) | 32 (4) | 16 (6) |
| P. aeruginosa K34-73 | 8 (10) | 8 (7) | 8 (<0.5) | 32 (4) | 8 (11) |
| P. aeruginosa K44-24 | 16 (5) | 8 (7) | 16 (<0.25) | 32 (4) | 16 (6) |
| P. aeruginosa 50692172 | 16 (5) | 8 (7) | 16 (<0.25) | 32 (4) | 16 (6) |
| P. aeruginosa 50692520 | 16 (5) | 16 (4) | 16 (<0.25) | 32 (4) | 16 (6) |
| K. pneumoniae K47-25* | 4 (19) | 4 (14) | 16 (<0.25) | 16 (8) | 8 (11) |
| K. pneumoniae K66-45 | 4 (19) | 4 (14) | 8 (<0.5) | 16 (8) | 4 (22) |
| K. pneumoniae 50531633* | 4 (19) | 4 (14) | 16 (<0.25) | 16 (8) | 8 (11) |
| K. pneumoniae 50625602 | 4 (19) | 4 (14) | 16 (<0.25) | 16 (8) | 16 (6) |
| K. pneumoniae 50667959 | 16 (5) | 4 (14) | 8 (<0.5) | 16 (8) | 4 (22) |
| A. baumanii K12-21 | 4 (19) | 4 (14) | 4 (<1) | 32 (4) | 8 (11) |
| A. baumanii K44-35 | 8 (10) | 4 (14) | 4 (<1) | 32 (4) | 8 (11) |
| A. baumanii K47-42 | 8 (10) | 4 (14) | 4 (<1) | 32 (4) | 8 (11) |
| A. baumanii K55-13 | 8 (10) | 8 (7) | 4 (<1) | 32 (4) | 8 (11) |
| A. baumanii K63-58* | 4 (19) | 4 (14) | 4 (<1) | 32 (4) | 8 (11) |

*Clinical isolates resistant to the antibiotic colistin.

Toxicity was determined against human RBCs, and a selectivity index (SI) was defined as the RBC $EC_{50}$ value divided by the MIC value against individual isolates. The antimicrobial potencies against the multi-resistant clinical isolates were as low as MIC 2-4 µg/ml for the most potent barbiturates and followed the same trends as against the antibiotic susceptible strains.

The most potent broad-spectrum barbiturates were the amine barbiturate 7(iii), and the guanidine barbiturates 8(i), 8(ii), 8(iii), and 8(v). It was evident that the guanidine group was efficient as the cationic group by the large number of highly potent guanidine barbiturates compared to amine barbiturates. However, several of the guanidine barbiturates displayed almost twofold higher RBC toxicity compared to analogous amine barbiturates. The interplay between the two different cationic groups and the seven different lipophilic side-chains thereby influenced both antimicrobial potency and RBC toxicity.

7(i) displayed low haemolytic activity ($EC_{50}$ 143 µg/ml) resulting in a good SI of 18-36 with respect to its activity against S. aurues, E. faecium and E. coli.

Among the three amine barbiturates 7(ii), 7(vi), and 7(iii) with 3,5-disubstituted benzylic side-chains, the super-bulky 7(iii) was most potent with MIC values of 2-16 µg/ml against all the 30 multi-resistant clinical isolates.

For the remaining two 3,5-disubstituted barbiturates, 7(ii) was more potent than 7(vi) showing that two bromine atoms as bulky benzylic substituents were more efficient than having two trifluoromethyl groups. However, the calculated C log P of 7(ii) was lower than the calculated C log P for the less potent 7(vi), showing that not only lipophilic effects of the side-chains affected antimicrobial potency, but possibly also electronic effects. The brominated barbiturate 7(ii) was very potent against S. aurues, E. faecium and E. coli with MIC values of 4-8 µg/ml, and by its high SI of 10-21 was one of the most promising amine barbiturates prepared.

The amine barbiturates 7(iv) and 7(v) contained naphthyl based side-chains, and both showed highest potency against the Gram-positive isolates of S. aurues and E. faecium with MIC values 4-16 µg/ml. The fluorine substituted barbiturate 7(v) was more potent than 7(iv) against isolates of E. faecium. The difference was one titre step of the concentration gradient used, but reflected also the higher side-chain C log P of 7(v) compared to 7(iv) (Table 2). Of importance was the very low haemolytic activity of both 7(iv) with $EC_{50}$ 243 µg/ml and 7(v) with $EC_{50}$ 160 µg/ml, which gave very high SI's of 20-40 against the Gram-positive isolates.

As discussed above, guanylation of the barbiturates resulted in both increased antimicrobial potency and haemolytic activity of series 8.

The larger guanidine group can form more intricate electrostatic and hydrogen-bonding interactions than a primary amine group, and thereby interact with both anionic and zwitterionic phospholipids. The increased antimicrobial activity and RBC toxicity may be explained by the guanidine groups ability to bind to both anionic phospholipids being the main constituent of bacterial membrane, and zwitterionic phospholipids being the main constituent in mammalian cell structure.

With respect to side-chain structures, the same order of potency was observed for the guanidine barbiturates of series 8 as for the amine barbiturates of series 7. However, the guanidine series 8 represented a major increase in antimicrobial activity against the Gram-negative multi-resistant clinical isolates compared to the amine series 7. The 4-substituted barbiturate 8(i) displayed MIC values of 4-8 µg/ml against the Gram-negative multi-resistant clinical isolates of K. pneumoniae and A. baumanii, as well as MIC values of 2-4 µg/ml against S. aurues, E. faecium and E. coli. This represented up to 4-fold improvement in antimicrobial activity compared to the analogous amine barbiturate 7(i). Also higher antimicrobial activity against P. aeruginosa (MIC: 8-16 µg/ml) for 8(i) was accomplished by changing the cationic group to guanidine.

The level of toxicity against human RBCs for the guanidine barbiturates of series 8 depended also on the specific side-chain structure in question. For the guanidine 8(i) twofold increased RBC toxicity was observed compared to the amine 7(i). However, the haemolytic activity of 8(i) was still low with $EC_{50}$ of 77 µg/ml resulting in high SI's of 19-39 with respect to its high potency against multi-resistant S. aurues, E. faecium and E. coli.

Of the two 3,5-disubstituted guanidine barbiturates 8(ii) and 8(iii) tested, 8(ii) was the overall most broad-spectrum barbiturate prepared throughout the study, and displayed MIC values of 2-16 µg/ml against all 30 multi-resistant clinical isolates of Gram-positive and Gram-negative bacteria. The haemolytic activity of 8(ii) ($EC_{50}$: 56 µg/ml) was lower than expected compared to the general twofold increase in toxicity observed for the guanidine barbiturates and the haemolytic toxicity of its analogous amine counterpart 7(ii) ($EC_{50}$: 83 µg/ml). Thus, the efficiency of the two bromine atoms as bulky substituents on the benzylic side-chains was once more demonstrated, and pointed to 8(ii) as one of the most promising broad-spectrum barbiturates prepared.

The super-bulky barbiturate 8(iii) was among the most potent derivatives prepared.

The antimicrobial potencies of the two naphthyl based guanidine barbiturates 8(iv) and 8(v), showed that the fluorinated 8(v) had highest broad-spectrum activity with MIC values of 2-16 µg/ml against all the 30 multi-resistant clinical isolates. The toxicity against human RBCs was also low for 8(v) ($EC_{50}$: 88 µg/ml) and comparable to the most promising brominated amine barbiturate 7(ii). Due to the high potency of 8(v) it also displayed a higher SI of 11-44 against S. aurues, E. faecium and E. coli, and was thereby the overall second most selective derivative against the multi-resistant clinical isolates of S. aureus (SI: 44) of all barbiturates prepared.

Barbiturate 8(v) was also among the most selective barbiturates against individual isolates of the Gram-negative bacteria. The less potent analogue 8(iv) showed MIC values of 8-16 µg/ml against S. aureus and E. faecium, and was thereby equipotent to its amine analogue 7(iv). The potency of 8(iv) against E. coli was higher than for 7(iv), but due to higher haemolytic activity the SI of the guanylated barbiturate 8(iv) was lower than for the amine barbiturate 7(iv). A stronger effect on RBC toxicity than antimicrobial activity was therefore observed by guanylation of 7(iv) to 8(iv).

Against the three clinical isolates of K. pneumoniae K47-25, K. pneumoniae 50531633, and A. baumanii K63-58 that display resistance against the last-resort cationic antibiotic colistin, all the investigated amphipathic barbiturates displayed antimicrobial activity in the same range as against the colistin susceptible clinical isolates. The mechanism of resistance is thought to involve altered LPS composition and charge that affects the binding and mechanism of colistin, but it seemed not to have any major impact on the binding and activity of the most potent present amphipathic barbiturates.

Chemicals and Equipment

All reagents and solvents were purchased from commercial sources and used as supplied with the exception of starting material 1-(Bromomethyl)-4-fluoronaphthalene, which was synthesized from the 4-Fluoro-1-naphthoic acid according to literature procedures.

Anhydrous DMF was prepared by storage over 4 Å ($4 \times 10^{-10}$ m) molecular sieves. Reactions were monitored by thin-layer chromatography (TLC) with Merck pre-coated silica gel plates (60 F254). Visualization was accomplished with either UV light or by immersion in potassium permanganate or phosphomolybdic acid (PMA) followed by light heating with a heating gun.

Purifications using normal phase flash chromatography were either done by normal column chromatography using Normalsil 60, 40-63 mm silica gel or by automated normal phase flash chromatography (Heptane/EtOAc) with the sample preloaded on a Samplet® cartridge belonging to a Biotage SP-1.

Purification of reactions by reversed-phase (RP) C18 column chromatography (water with 0.1% TFA/acetonitrile with 0.1% TFA) was also executed on an automated purification module with the sample preloaded on a Samplet® cartridge. Analytical RPHPLC was carried out on a Waters 2695 Separations Module equipped with an XBridge™ C18 5 μm, 4.6 mm×250 mm column and analysed at wavelengths 214 and 254 nm with a Waters 996 PDA detector spanning from wavelengths 210 to 310 nm. The derivatives were eluted with a mobile phase consisting of water and acetonitrile, both containing 0.1% TFA. The gradient started at 10% acetonitrile (3 min), followed by a linear gradient to 90% acetonitrile over 17 min. The flow rate was 1 mL min-1. NMR spectra were obtained on a 400 MHz Bruker Avance III HD equipped with a 5 mm SmartProbe BB/1H (BB=19F, 31P-15N). Data are represented as follows: chemical shift, multiplicity (s=singlet, d=doublet, t=triplet, q=quartet, p=pentet, h=heptet, m=multiplet), coupling constant (J, Hz) and integration.

Chemical shifts (δ) are reported in ppm relative to the residual solvent peak ($CDCl_3$: δH 7.26, and δC 77.16; CD3OD: δH 3.31 and δC 49.00). Positive and negative ion electrospray ionization mass spectrometry (ESI-MS) was conducted on a Thermo electron LTQ Orbitrap XL spectrometer.

Synthesis

Established methods for the synthesis of substituted barbiturates include the condensation of alkylated malonate esters with urea, cyclization with N-alkylated urea and diethyl malonate, Knoevenagel condensation of barbituric acid and aldehydes or ketones, and alkylation of barbituric acid. However, the latter procedure is unselective with regards to alkylation of the 1, 3 and 5 positions. The present inventors have found that the condensation of dialkylated malonate esters with urea followed by N-alkylation was the most successful strategy.

As shown in Scheme 1, Symmetrically disubstituted malonates 3(i)-(vi) were obtained from diethyl malonate 2 by dialkylation with the appropriate benzylic halides, and were subsequently cyclized with urea by treatment with $NaH$ or $K_2CO_3$ in DMF to provide 4(i)-(vi) in yields of 70-92%. Dry conditions were imperative to the yield. Cyclisation of malonate 3(vi) gave low yields (27%) due to decarboxylation under the reaction conditions. The 5,5-disubstituted barbiturates 4(i)-(vi) were alkylated with an excess of 1,4-dibromobutane under basic conditions ($K_2CO_3$ in DMF) to give N,N"-dialkylated alkyl bromide barbiturates 5(i)-(vi) in 40-96% yield. These were converted to the corresponding azides 6(i)-(vi) with $NaN_3$ (2-3 equiv.) in DMF (68-100% yield). Reduction of the azides to amines with $NaBH_4$ and a catalytic amount of a dithiol, and subsequent Boc-protection provided Boc-protected diamines after purification by flash chromatography. Deprotection with TFA provided the target amine barbiturates 7(i)-(vi) (>95% purity as determined by analytical C18 reversed phase HPLC). The amine barbiturates 7(i)-(v) were guanylated with N-Boc-1H-pyrazole-1-carboxamidine in THF and purified before the Boc-protecting group was removed. Purification by C18 reversed phase flash chromatography gave the TFA salts of the target guanylated barbiturates 8(i)-(v) with >95% purity.

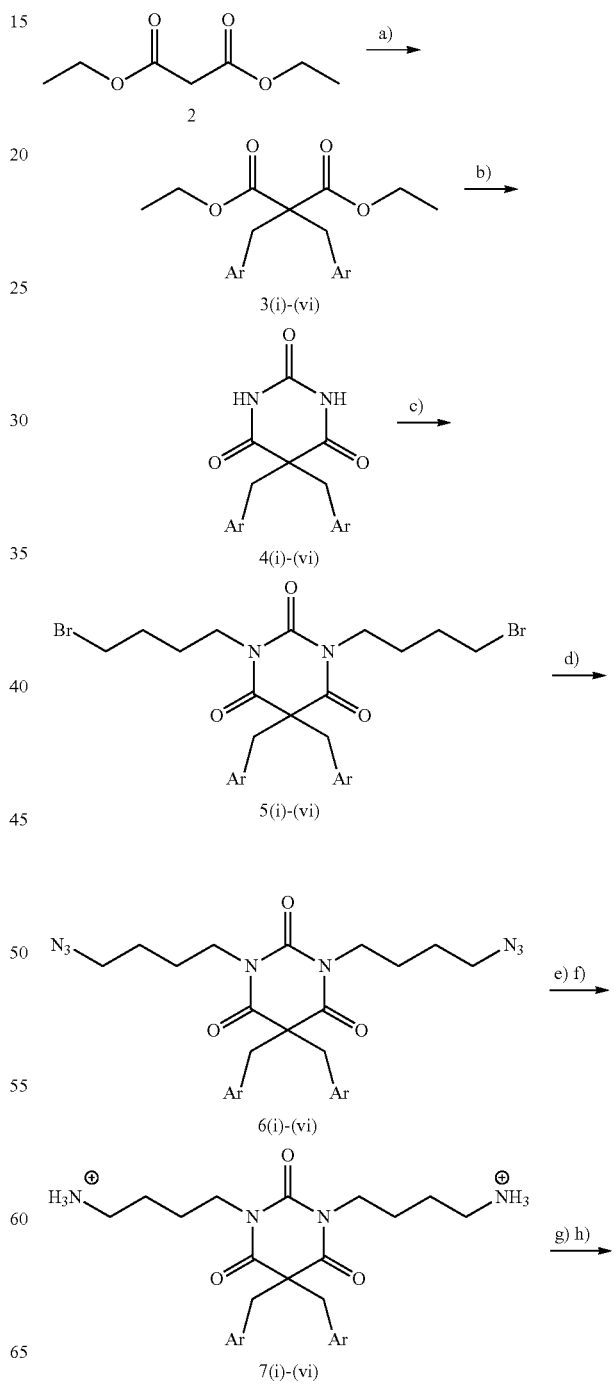

Scheme 1.

19

-continued

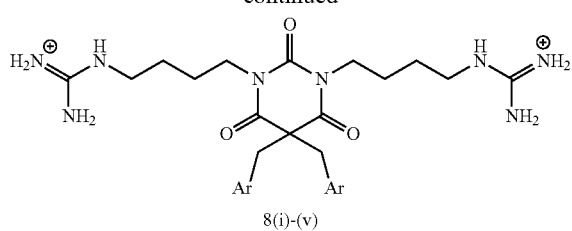

8(i)-(v)

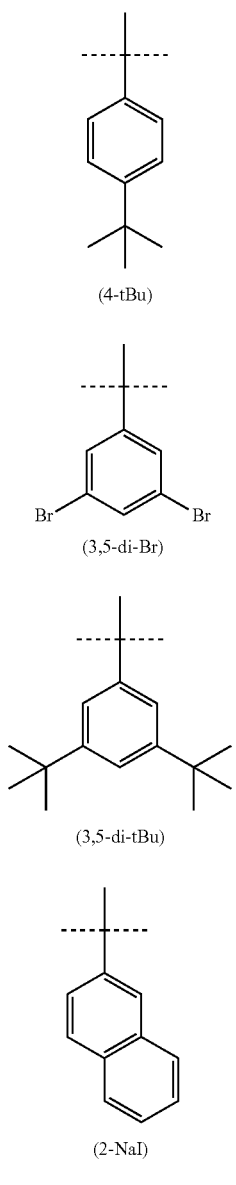

(4-tBu)

(3,5-di-Br)

(3,5-di-tBu)

(2-Nal)

(4-F-1-Nal)

20

-continued

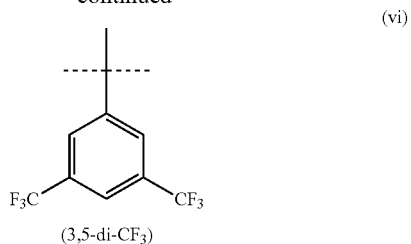

(3,5-di-CF$_3$)

Conditions: a) Conditions: a) ArCH$_2$Br, K$_2$CO$_3$ or NaH, DMF, R.T.; b) 10 equiv. urea (dry), NaH, DMF (dry), R.T.; c) 10 equiv. 1,4-dibromobutane, 4 equiv. K$_2$CO$_3$, DMF (dry), R.T., 18-48 h; d) 3 equiv. NaN$_3$, DMF (dry); e) NaBH$_4$, 1,3-dimercaptopropane, THF:isopropanol 1:1, R.T.; f) i. Boc$_2$O, R.T., ii. CH$_2$Cl$_2$:TFA. h) i. N-Boc-1H-pyrazole-1-carboxamidine, THF, R.T., ii. CH$_2$Cl$_2$:TFA.

Detailed Synthesis
Dialkylated Malonate Ester—3(i)-(vi)
General Procedure:

To a stirred solution of diethyl malonate in DMF (≈100 mg/mL) over Cs$_2$CO$_3$ (2.1-2.2 equiv.) or K$_2$CO$_3$ (3 equiv.) was added the alkyl halide (2 equiv.). The reaction was kept stirring at r.t. over night. The reaction mixture was diluted with EtOAc (30 mL) and washed with water (25 mL), aqu. 5% LiCl sol. (3×25 mL) and brine (25 mL). The organic phase was dried over Na$_2$SO$_4$, filtered and concentrated. The crude product was dissolved in CH$_2$Cl$_2$ (20 mL) and adsorbed on Celite. The product was purified on a silica column using 1-5% EtOAc in pentane as mobile phase.

Diethyl 2,2-bis(4-tert-butylbenzyl)malonate-3(i)

According to the general procedure, a stirred solution of diethyl malonate (3.43 g, 21.4 mmol) in DMF (25 mL) over K$_2$CO$_3$ (8.8 g, 64.2 mmol) was added 1-(bromomethyl)-4-tert-butylbenzene (10 g, 44 mmol). The reaction was kept stirring at r.t. overnight. The reaction mixture was diluted with EtOAc (80 mL) and washed with water (3×50 mL), aqu. 5% LiCl sol. (50 mL) and brine (50 mL). The organic phase was dried over Na$_2$SO$_4$, filtered and concentrated. The crude product was dissolved in dichloromethane (20 mL) and adsorbed on to Celite. The product was purified on a silica column using 1-5% EtOAc in pentane as mobile phase to yield 3(i) (8.80 g, 90%) as a white solid.

1H NMR (400 MHz, CDCl$_3$): δ 7.28 (d, J=8.3 Hz, 4H), 7.11 (d, J=8.4 Hz, 4H), 4.10 (q, J=7.1 Hz, 4H), 3.19 (s, 4H), 1.30 (s, 18H), 1.14 (t, J=7.1 Hz, 6H).

13i) NMR (101 MHz, CDCl$_3$): δ 171.2, 149.7, 133.4, 129.9, 125.2, 61.2, 60.4, 38.6, 34.5, 31.5, 14.0.

HRMS-ESI: C29H40NaO4+[M+Na]+ calcd: 475.2818, found: 475.2795.

Diethyl 2,2-bis(3,5-dibromobenzyl)malonate-3(ii)

According to the general procedure, a stirred solution of diethyl malonate (460 mg, 2.9 mmol) in DMF (5 mL) over Cs$_2$CO$_3$ (2.0 g, 6.37 mmol) was added 1,3-dibromo-5-(bromomethyl)benzene (2 g, 6.0 mmol). The reaction was kept stirring at r.t. over night. The reaction mixture was diluted with EtOAc (30 mL) and washed with water (25 mL), aqu. 5% LiCl sol. (3×25 mL) and brine (25 mL). The organic phase was dried over Na$_2$SO$_4$, filtered and concentrated. The crude product was dissolved in CH$_2$Cl$_2$ (20 mL) and adsorbed on Celite. The product was purified on a silica column using 1-5% EtOAc in pentane as mobile phase to yield 3(ii) (1.17 g, 61%) as a white solid.

1H NMR (400 MHz, CDCl$_3$): δ 7.56 (t, J=1.8 Hz, 2H), 7.24 (d, J=1.8 Hz, 4H), 4.15 (q, J=7.1 Hz, 4H), 3.11 (s, 4H), 1.20 (t, J=7.2 Hz, 6H).

13i) NMR (101 MHz, CDCl$_3$): δ 170.0, 139.9, 132.8, 132.0, 122.7, 61.9, 60.0, 39.3, 13.9.

HRMS-ESI: C21H20Br4NaO4+[M+Na]+ calcd: 674.7987, found: 674.7961.

Diethyl 2,2-bis(naphtalen-2-yl-methyl)malonate-3(iv)

To a stirred solution of diethyl malonate (3.44 g, 21.5 mmol) in 15 mL CH$_2$Cl$_2$ at 0° C. was added DBU (3.3 mL, 22.6 mmol). Reaction mixture was stirred for 5 min before 2-(bromomethyl)naphtalene (5 g, 22.6 mmol) was added. The reaction was allowed to reach r.t. and was stirred over night. The reaction was concentrated and the crude product isolated as a brown oil. The oil was dissolved in EtOAc (30 mL) and washed with water (2×30 mL), 10% citric acid (30 mL), 10% NaHCO$_3$ (30 mL) and brine (30 mL). The organic phase was dried over Na$_2$SO$_4$, filtered and concentrated affording 4.83 g of almost pure monoalkylated diethyl malonate. To a suspension of NaH (774 mg, 32.2 mmol) in dry THF (15 mL) at 0° C. was added diethyl 2-(naphthalen-2-ylmethyl)malonate (4.8 g) dropwise as a solution in THF (15 mL). The resulting mixture was stirred for 10 min before 2-naphtyl methyl bromide (5 g, 22.6 mmol) was added. The reaction was allowed to reach r.t. and was stirred over night. The reaction mixture was cooled in icebath, the excess of NaH was quenched with 10% citric acid solution and the reaction mixture concentrated. The crude product was then dissolved in EtOAc and washed with 10% citric acid sol. (3×30 mL), 10% NaHCO$_3$ sol. (2×30 mL) and brine (30 mL). The organic phase was dried over Na$_2$SO$_4$, filtered and concentrated to yield crude 3(iv) (7.35 g, 78%).

1HNMR (400 MHz, CDCl$_3$): δ 7.85-7.80 (m, 2H), 7.77 (d, J=8.1 Hz, 4H), 7.65 (d, J=1.7 Hz, 2H), 7.49-7.43 (m, 4H), 7.32 (dd, J=8.5, 1.7 Hz, 2H), 4.14 (q, J=7.1 Hz, 4H), 3.45 (s, 4H), 1.14 (t, J=7.1 Hz, 6H). HRMS-ESI: C29H29O4+[M+H]+ calcd: 441.2060, found: 441.2059.

Diethyl 2,2-bis((4-fluoronaphtalen-1-yl-methyl)malonate-3(v)

According to the general procedure, a stirred solution of diethyl malonate (1.3 g, 8.16 mmol) in DMF (10 mL) over K$_2$CO$_3$ (3.36 g, 24.3 mmol) was added 4-F-napht-1-yl Bromo methane (4 g, 16.7 mmol). The reaction was kept stirring at r.t. over night. The reaction mixture was diluted with EtOAc (30 mL) and washed with water (3×20 mL), aqu. 5% LiCl sol. (20 mL) and brine (20 mL). The organic phase was dried over Na$_2$SO$_4$, filtered and concentrated. In a round bottomed flask the brown solid crude product was dissolved in warm EtOH, capped with alumina foil and left for 4 days at r.t. Upon standing for an hour the product crashed out of the brown solution as a white solid (1.6 g, 41%).

1H NMR (400 MHz, CDCl$_3$): δ 8.18-8.08 (m, 2H), 8.05-7.95 (m, 2H), 7.57-7.46 (m, 4H), 7.36 (dd, J=8.0, 5.5 Hz, 2H), 7.04 (dd, J=10.2, 8.0 Hz, 2H), 3.81 (s, 4H), 3.75 (q, J=7.2 Hz, 4H), 0.85 (t, J=7.1 Hz, 6H). 13i) NMR (101 MHz, CDCl$_3$): δ 171.3, 158.1 (d, J=251.4 Hz), 134.2 (d, J=4.2 Hz), 128.9 (d, J=4.6 Hz), 127.6 (d, J=8.2 Hz), 126.8, 125.9 (d, J=2.1 Hz), 124.1-123.9 (m), 121.2 (d, J=6.0 Hz), 108.9 (d, J=19.7 Hz), 61.5, 59.8, 35.5, 13.6. HRMS-ESI: C29H26(iv)2NaO4+[M+Na]+ calcd: 499.1691, found: 499.1689. 4.2.2.

Diethyl 2,2-bis(3,5-bis(trifluoromethyl)benzyl)malonate-3(vi)

According to the general procedure, a stirred solution of DEM (490 mg, 3.1 mmol) in DMF (5 mL) over Cs$_2$CO$_3$ (2.2 g, 6.83 mmol) was added 1-(bromomethyl)-3,5-bis(trifluoromethyl) benzene (2 g, 6.51 mmol). The reaction was kept stirring at r.t. over night. The reaction mixture was diluted with EtOAc (30 mL) and washed with water (25 mL), aqu. 5% LiCl sol. (3×25 mL) and brine (25 mL). The organic phase was dried over Na$_2$SO$_4$, filtered and concentrated. The crude product was dissolved in CH$_2$Cl$_2$ (20 mL) and adsorbed on Celite. The product was purified on a silica column using 1-5% EtOAc in pentane as mobile phase to yield 3(vi) (0.89 g, 63%) as a white solid. 1H NMR (400 MHz, CDCl$_3$): δ 7.79 (s, 2H), 7.71-7.54 (m, 4H), 4.10 (q, J=7.1 Hz, 4H), 3.32 (s, 4H), 1.13 (t, J=7.1 Hz, 6H).

13i) NMR (101 MHz, CDCl$_3$): δ 169.8, 138.5, 131.8 (q, J=33.3 Hz), 130.9-130.2 (m), 123.3 (q, J=272.7 Hz), 121.5 (p, J=3.9 Hz), 62.2, 60.3, 40.3, 13.8. HRMS-ESI: C25H19F12O4−[M−H]− calcd: 611.1098, found: 611.1097.

5,5-bis(4-tert-butylbenzyl)pyrimidin-2,4,6(1H,3H,5H)-trione-4(i)

To a stirred solution of urea (6.63 g, 110 mmol) at r.t. in anhydrous DMF (20 mL) was added NaH (660 mg, 27.5 mmol) and the reaction was stirred for 5 min. A solution of 3(i) (5(v), 11 mmol) in anhydrous DMF (20 mL) was added dropwise to the reaction mixture and the reaction was stirred over night. The reaction mixture was diluted with EtOAc (20 mL) and washed with 10% citric acid (100 mL), 10% NaHCO$_3$ (50 mL), brine (50 mL), water (20 mL), and brine (2×50 mL). The organic phase was dried over Na$_2$SO$_4$, filtered and concentrated. The crude product was purified with automated flash chromatography (heptane/EtOAc) affording 4.09 g (88%) of the product 4(i) as a white powder.

1H NMR (400 MHz, MeOD4): δ 7.26 (d, J=7.7 Hz, 2H), 7.05 (d, J=7.6 Hz, 2H), 3.31 (s, 6H, overlap MeOD), 1.24 (s, 18H). 13i) NMR (101 MHz, MeOD4): δ 174.2, 151.5*, 133.5, 130.4, 126.4, 61.4, 45.0, 35.3, 31.7. *assumed overlap of two signals HRMS-ESI: C26H31N2O3−[M−H]− calcd: 419.2340, found: 419.2335.

5,5-bis(3,5-dibromobenzyl)pyrimidine-2,4,6-(1H,3H,5H)-trione-4(ii)

To a stirred solution of urea (1.83 g, 2.79 mmol) in anhydrous DMF (15 mL) was added NaH (183 mg, 7.6 mmol) and the resulting solution was stirred for 10 min before 3(ii) (2.0 g, 3.05 mmol) was added. The resulting mixture was stirred over night. The reaction was diluted with EtOAc (50 mL), washed with 10% citric acid sol. (3×25 mL), 10% NaHCO$_3$ (2×30 mL), and brine (30 mL). The organic phase was dried over Na$_2$SO$_4$, filtered and concentrated. The white solid was dissolved in chloroform (25 mL) and concentrated again, purified by flash chromatography to yield 4(ii) (1.52 g, 88%).

1H NMR (400 MHz, CDCl$_3$): δ 7.82 (NH, s, 2H), 7.58 (t, J=1.8 Hz, 2H), 7.21 (d, J=1.5 Hz, 4H), 3.32 (s, 4H). 13i) NMR (101 MHz, CDCl$_3$): δ 170.0, 146.4, 137.7, 134.2, 131.5, 123.6, 59.9, 43.4. HRMS-ESI: C18H11 79Br4N2O3−[M−H]− calcd: 618.7509, found: 618.7501.

5,5-bis((naphtalen-2-yl)methyl)pyrimidine-2,4,6(1H,3H,5H)-trione-4(iv)

NaH (9 mg, 0.37 mmol) was added to a stirred solution of urea (91 mg, 1.49 mmol) in anhydrous DMF (3 mL) at r.t.

The reaction mixture was left to stir for 10 min before 3(iv) (66 mg, 0.15 mmol) was added slowly and the reaction was left to stir over night. The reaction mixture was diluted with EtOAc (20 mL) and washed with water (4×20 mL) followed by brine (20 mL). The organic phase was dried over $Na_2SO_4$, filtered and concentrated. The crude product was dissolved in $CHCl_3$ and adsorbed onto celite before purification on a silica column using 0-5% EtOAc in $CHCl_3$ as mobile phase to yield 4(iv) (50 mg, 82%).

1H NMR (400 MHz, CD3OD): δ 7.76-7.70 (m, 4H), 7.69 (d, J=8.6 Hz, 2H), 7.62 (s, 2H), 7.44-7.36 (m, 4H), 7.26 (dd, J=8.4, 1.7 Hz, 2H), 3.60 (s, 4H). 13i) NMR (101 MHz, CD3OD): δ 173.2, 149.5, 133.8, 133.1, 132.8, 129.1, 128.7, 128.1, 127.9, 127.8, 126.6, 126.4, 60.8, 45.1. HRMS-ESI: C26H19N2O3−[M−H]− calcd: 407.1417, found: 407.1400.

5,5-bis((4-fluoronaphtalene-1-yl)methyl)pyrimidine-2,4,6(1H,3H,5H)-trione-4(v)

To a stirred solution of urea (630 mg, 10.49 mmol) in anhydrous DMF (4 mL) was added NaH (76 mg, 3.16 mmol) and the resulting solution was stirred for 10 min before 3(v) (500 mg, 1.05 mmol) was added slowly. The resulting mixture was stirred over night. The reaction mixture was diluted with 25 mL EtOAc and washed with 4×50 mL water followed by 20 mL brine. The organic phase was dried over $Na_2SO_4$, filtered and concentrated. The crude product was dissolved in $CHCl_3$ and adsorbed onto celite before purification on a silica column using 0-5% EtOAc in $CHCl_3$ as mobile phase to yield 4(v) (430 mg, 92%).

1H NMR (400 MHz, $CDCl_3$): δ 8.23 (d, J=8.5 Hz, 2H), 8.14-8.04 (m, 2H), 7.64-7.49 (m, 4H), 7.46 (s, 2H), 7.29-7.26 (m, 2H), 7.00 (dd, J=9.9, 8.1 Hz, 2H), 4.05 (s, 4H). 13i) NMR (101 MHz, $CDCl_3$): δ 171.4, 158.7 (d, J=253.3 Hz), 146.8, 133.3 (d, J=4.5 Hz), 128.0 (d, J=8.7 Hz), 127.4, 126.7 (d, J=4.7 Hz), 126.5 (d, J=1.9 Hz), 124.4-124.1 (m), 121.3 (d, J=6.2 Hz), 109.1 (d, J=20.1 Hz), 59.8, 40.0. HRMS-ESI: C26H19N2O3−[M−H]− calcd: 407.1401, found: 407.1414 4.2.3.

5,5-bis(3,5-bis(trifluoromethyl)benzyl)pyrimidine-2,4,6(1H,3H,5H)-trione-4(vi)

To a solution of urea (1.3 g, 21.6 mmol) in 20 mL anhydrous DMF was added NaH (128 mg, 5.3 mmol) and the resulting solution was stirred for 10 min before 3(vi) (1.0 g, 1.7 mmol) was added. The resulting mixture was stirred over night. The reaction was diluted with EtOAc 9 (50 mL), washed with 10% citric acid sol. (3×30 mL), 10% $NaHCO_3$ (2×20 mL), and brine (30 mL). The organic phase was dried over $Na_2SO_4$, filtered and concentrated. The crude was purified by automated flash chromatography to yield the product 4(vi) (0.27 g, 27%) as white powder.

1H NMR (400 MHz, $CDCl_3$): δ 7.82 (s, 2H), 7.73 (s, 2H), 7.62-7.57 (m, 4H), 3.57 (s, 4H). 13i) NMR (101 MHz, $CDCl_3$): δ 169.8, 146.1, 136.3, 132.6 (q, J=33.6 Hz), 130.4-129.7 (m), 122.0 (q, J=272.8 Hz), 122.9-122.2 (m), 59.9, 43.5. HRMS-ESI: C22H11F12N2O3−[M−H]− calcd: 579.0584, found: 579.0583.

1,3-bis(4-bromobutyl)-5,5-bis(4-tert-butylbenzyl)-pyrimidine-2,4,6(1H,3H,5H)-trione-5(i)

To a stirred solution of 4(i) (3.88 g, 9.23 mmol) at r.t. in DMF (50 mL) was added $K_2CO_3$ (5.12 g, 37 mmol) and 1,4-dibromobutane (10.9 mL, 92.5 mmol). The reaction mixture was stirred over night. The reaction mixture was diluted with EtOAc (100 mL) and washed with water (100 mL). The crude product was purified with automated flash chromatography affording the product 5(i) (2.60 g, 40%) as a white powder.

1H NMR (400 MHz, $CDCl_3$): δ 7.22 (d, J=7.8 Hz, 4H), 6.98 (d, J=7.9 Hz, 4H), 3.60 (t, J=6.9 Hz, 4H), 3.41 (s, 4H), 3.33 (t, J=6.4 Hz, 4H), 1.56 (p, J=7.3 Hz, 4H), 1.42 (p, J=7.7 Hz, 4H), 1.25 (s, 18H). 13i) NMR (101 MHz, $CDCl_3$): δ 170.9, 150.7, 149.9, 131.9, 129.2, 125.5, 60.7, 45.0, 40.7, 34.5, 32.9, 31.4, 29.5, 26.2. HRMS-ESI: C34H46 79Br2N2NaO3+[M+Na]+ calcd: 711.1774, found: 711.1773.

1,3-bis(4-bromobutyl)-5,5-bis(3,5-dibromobenzyl)-pyrimidine-2,4,6-(1H,3H,5H)-trione-5(ii)

To a stirred solution of 4(ii) (300 mg, 0.48 mmol) in DMF (6 mL) was added $K_2CO_3$ (265 mg, 1.92 mmol) and 1,4-dibromobutane (0.57 mL, 4.81 mmol). The reaction was stirred until completion was indicated by TLC (5% EtOAc in $CHCl_3$). The reaction mixture was diluted with EtOAc (25 mL) and the $K_2CO_3$ was filtered off. The organic phase was washed with 10% citric acid sol. (30 mL), $NaHCO_3$ (30 mL), water (3×30 mL) and brine (30 mL), dried with $Na_2SO_4$, filtered and concentrated resulting in an oil that slowly turned into white crystals. The crude product was dissolved in $CHCl_3$ (30 mL) and adsorbed onto celite before purification on silica column using pentane: $CH_2Cl_2$ (7:3 to 1:1) to yield 5(ii) (347 mg, 80%) as white powder.

1H NMR (400 MHz, $CDCl_3$): δ 7.54 (d, J=1.8 Hz, 2H), 7.14 (d, J=1.7 Hz, 4H), 3.65 (t, J=7.4 Hz, 4H), 3.38 (t, J=6.7 Hz, 4H), 3.33 (s, 4H), 1.77-1.61 (m, 4H), 1.58-1.43 (m, 4H). 13i) NMR (101 MHz, $CDCl_3$): δ 169.9, 149.1, 138.4, 133.9, 131.3, 123.4, 59.9, 44.2, 41.3, 32.7, 30.0, 26.7. HRMSESI: C26H26 79Br3 81Br3ClN2O3−[M+Cl]− calcd: 928.6671, found: 928.6669.

1,3-bis(4-bromobutyl)-5,5-bis(3,5-di-tert-butylbenzyl)-pyrimidine-2,4,6(1H,3H,5H)-trione-5(iii)

To a stirred solution 10 of 4(iii) (0.86 g, 1.62 mmol) in DMF was added $K_2CO_3$ (1.2 g, 8.9 mmol). The reaction mixture was stirred for 5 min before addition of 1,4-dibromobutane (1.76 mL, 14.8 mmol). The reaction was stirred until completion was indicated by TLC (5% EtOAc in $CHCl_3$). Then the reaction mixture was diluted with EtOAc (15 mL) and the $K_2CO_3$ was filtered off. The organic phase was washed with 10% citric acid sol. (30 mL), $NaHCO_3$ (30 mL), water (3×30 mL) and brine (30 mL), dried with $Na_2SO_4$, filtered and concentrated. The crude was purified by automated flash chromatography to yield the product 5(iii) (0.64 g, 74%).

1H NMR (400 MHz, $CDCl_3$): δ 7.26 (t, J=1.9 Hz, 2H), 6.89 (d, J=1.8 Hz, 4H), 3.59* (t, J=7.5 Hz, 4H), 3.46 (s, 4H), 3.23 (t, J=6.7 Hz, 4H), 1.51 (p, J=6.8 Hz, 4H), 1.35-1.23 (m, 40H). 13i) NMR (101 MHz, $CDCl_3$): δ 171.0, 151.1, 150.0, 134.4, 123.7, 121.5, 60.5, 46.5, 40.9, 34.8, 32.4, 31.6, 29.7, 26.5. *distorted triplet. HRMS-ESI: C42H62 79Br2KN2O3+[M+K]+ calcd: 839.2759, found: 839.2725.

1,3-bis(4-bromobutyl)-5,5-bis(naphtalen-2-yl-methyl)-pyrimidine-2,4,6(1H,3H,5H)-trione-5(iv)

To a stirred suspension of 4(iv) (200 mg, 0.49 mmol) and $K_2CO_3$ (273 mg, 1.95 mmol) in DMF (4 mL) was added 1,4-dibromobutane (0.57 mL, 4.9 mmol). The reaction was stirred until completion was indicated by TLC (5% EtOAc in CHCl$_3$). Then the reaction mixture was diluted with EtOAc (25 mL) and the K$_2$CO$_3$ was filtered off. The organic phase was washed with 10% citric acid sol. (30 mL), NaHCO$_3$ (30 mL), water (3×30 mL), and brine (30 mL), dried with Na$_2$SO$_4$, filtered and concentrated. The crude product was dissolved in CHCl$_3$ (30 mL) and adsorbed onto celite before purification on silica column using 0-5% EtOAc in CHCl$_3$ to yield 5(iv) (347 mg, 80%) as white powder.

1H NMR (400 MHz, CDCl$_3$): δ 7.75 (dd, J=9.4, 6.4 Hz, 4H), 7.70 (d, J=8.4 Hz, 2H), 7.57 (s, 2H), 7.48-7.42 (m, 4H), 7.18 (dd, J=8.5, 1.7 Hz, 2H), 3.68 (s, 4H), 3.53 (t, J=6.7 Hz, 4H), 2.99 (t, J=6.2 Hz, 4H), 1.35-1.19 (m, 8H). 13i) NMR (101 MHz, CDCl$_3$): δ 170.9, 149.6, 133.3, 132.7, 132.5, 128.8, 128.5, 127.8, 127.7, 127.2, 126.6, 126.3, 60.8, 45.8, 40.9, 32.8, 29.5, 26.3. HRMSESI: C34H34 79Br2N2NaO3+[M+Na]+ calcd: 699.0827, found: 699.0839.

1,3-bis(4-bromobutyl)-5,5-bis(4-F-naphtalene-1-ylmethyl) pyrimidine-2,4,6(1H,3H,5H)-trione-5(v)

To a stirred suspension of 4(v) (242 mg, 0.54 mmol) and K$_2$CO$_3$ (300 mg, 2.17 mmol) in DMF (5 mL) was added 1,4-dibromobutane (0.64 mL, 5.4 mmol). The reaction was checked with TLC (CHCl$_3$ Rf product 0.74, Rf starting material 0.11) and when no traces of starting material was visible the reaction mixture was diluted with EtOAc (25 mL) and the K$_2$CO$_3$ filtered off. The organic phase was washed with 10% citric acid sol. (30 mL), NaHCO$_3$ (30 mL), water (3×30 mL) and brine (30 mL) dried with Na$_2$SO$_4$, filtered and concentrated yielding the crude as an oil. The crude product was dissolved in CHCl$_3$ (30 mL) and adsorbed onto celite before purification on silica column using CHCl$_3$ as mobile phase to yield 5(v) (237 mg, 61%) as a white solid.

1H NMR (400 MHz, CDCl$_3$): δ 8.23 (d, J=8.6 Hz, 2H), 8.08 (d, J=8.3 Hz, 2H), 7.63 (t, J=7.7 Hz, 2H), 7.54 (t, J=7.6 Hz, 2H), 7.23 (dd, J=8.0, 5.5 Hz, 2H), 7.00 (dd, J=9.8, 8.1 Hz, 2H), 4.06 (s, 4H), 3.33 (t, J=7.2 Hz, 4H), 3.05 (t, J=6.6 Hz, 4H), 1.34-1.12 (m, 4H), 1.08-0.90 (m, 4H). 13i) NMR (101 MHz, CDCl$_3$): δ 170.96, 158.5 (d, J=253.3 Hz), 149.4, 133.2 (d, J=4.4 Hz), 128.0 (d, J=8.4 Hz), 127.4 (d, J=4.7 Hz), 127.2, 126.4 (d, J=2.1 Hz), 124.8 (d, J=2.7 Hz), 124.1 (d, J=15.7 Hz), 121.1 (d, J=6.0 Hz), 108.9 (d, J=20.0 Hz), 60.0, 40.9, 40.7, 32.7, 29.3, 25.9. HRMSESI: C34H32 79Br2F2N2NaO3+[M+Na]+ calcd: 735.0639, found: 735.0622. 4.2.4.

1,3-bis(4-bromobutyl)-5,5-bis(3,5-bis(trifluoromethyl)-benzyl)pyrimidine-2,4,6(1H,3H,5H)-trione-5(vi)

To a stirred solution of 4(vi) (0.864 g, 1.57 mmol) in DMF (20 mL) was added K$_2$CO$_3$ (1.233 g, 8.93 mmol) and 1,4-dibromobutane (1.76 mL, 14.9 mmol). The reaction mixture was stirred for 48 h, diluted with EtOAc (30 mL) and washed with water (3×20 mL), 5% LiCl sol. (3×20), and brine (20 mL). The crude product was purified with automated flash chromatography to afford 5(vi) (0.64 g, 50%) as a white powder.

1H NMR (400 MHz, CDCl$_3$): δ 7.79 (s, 2H), 7.53 (s, 4H), 3.59 (s, 4H), 3.57-3.51 (m, 4H), 3.26 (t, J=6.8 Hz, 4H), 1.67-1.55 (m, 4H), 1.43-1.29 (m, 4H). 13i) NMR (101 MHz, CDCl$_3$): δ 169.4, 148.4, 136.9, 132.2 (q, J=33.6 Hz), 130.0-129.4 (m), 122.9 (q, J=272.9 Hz), 122.1 (p, J=3.8 Hz), 59.7, 44.3, 41.1, 31.7, 29.6, 26.1. HRMS-ESI: C30H26 79Br3F12N2O3−[M+Br]− calcd: 926.9308, found: 926.9308.

1,3-bis(4-azidobutyl)-5,5-bis(4-tert-butylbenzyl)-pyrimidine-2,4,6(1H,3H,5H)-trione-6(i)

To a stirred solution of bromide 5(i) (2.40 g, 3.47 mmol) in DMF (15 mL) was added NaN$_3$ (678 mg, 10.4 mmol) and stirred for 18 h. The reaction mixture was diluted with EtOAc (50 mL) and washed with water (4×50 mL). The organic phase was dried over Na$_2$SO$_4$, filtered and concentrated. The crude product 6(i) was isolated as a clear oil (2.16 g, 100%).

1H NMR (400 MHz, CDCl$_3$): δ 7.20 (d, J=7.7 Hz, 4H), 6.97 (d, J=7.8 Hz, 4H), 3.59 (s, 4H), 3.40 (s, 4H), 3.21 (s, 4H), 1.37-1.28 (m, 8H), 1.24 (s, 18H). 13i) NMR (101 MHz, CDCl$_3$): δ 171.0, 150.8, 150.0, 132.0, 129.3, 125.5, 60.7, 50.9, 45.1, 41.1, 34.6, 31.4, 26.0, 24.8. HRMS-ESI: C34H46N8O3Na+[M+Na]+ calcd: 637.3577, found: 637.3583.

1,3-bis(4-azidobutyl)-5,5-bis(3,5-dibromobenzyl)pyrimidine-2,4,6-(1H,3H,5H)-trione-6(ii)

To a stirred solution of 5(ii) (239 mg, 0.26 mmol) in DMF (3 mL) was added NaN$_3$ (52 mg, 0.8 mmol). The reaction was stirred until completion was indicated by TLC (5% EtOAc in CHCl$_3$). Then the reaction mixture was diluted with EtOAc (15 mL) and washed with water (2×20 mL). The organic phase was dried over Na$_2$SO$_4$, filtered and concentrated. The crude product was dissolved in CHCl$_3$ and adsorbed onto celite before purification on silica column using 0-5% EtOAc in CHCl$_3$ to yield 6(ii) (194 mg, 91%).

1H NMR (400 MHz, CDCl$_3$): δ 7.54 (s, 2H), 7.14 (s, 4H), 3.73-3.58 (m, 4H), 3.33 (s, 4H), 3.31-3.22 (m, 4H), 1.58-1.29 (m, 8H). 13i) NMR (101 MHz, CDCl$_3$): δ 169.9, 149.1, 138.4, 133.8, 131.4, 123.3, 59.9, 50.9, 44.2, 41.6, 26.1, 25.3. HRMS-ESI: C26H26 79Br4(ii) 1N8O3−[M+Cl]− calcd: 848.8555, found: 848.8564.

1,3-bis(4-azidobutyl)-5,5-bis(3,5-di-tert-butylbenzyl)pyrimidine-2,4,6-(1H,3H,5H)-trione-6(iii)

To a stirred solution of 5(iii) (630 mg, 11 0.78 mmol) in DMF (10 mL) was added NaN$_3$ (140 mg, 2.15 mmol). The reaction was stirred over night. When full conversion was reached according to MS, the reaction mixture was diluted with EtOAc (50 mL) and washed with water 4×50 mL. The organic phase was dried over Na$_2$SO$_4$, filtered and concentrated affording the crude product 6(iii) (463 mg, 80%).

1H NMR (400 MHz, CDCl$_3$): δ 7.25 (t, J=1.9 Hz, 2H), 6.87 (d, J=1.7 Hz, 4H), 3.56 (t, J=7.2 Hz, 4H), 3.45 (s, 4H), 3.14 (t, J=6.5 Hz, 4H), 1.25 (s, 44H). 13i) NMR (101 MHz, CDCl$_3$): δ 171.1, 151.1, 150.0, 134.4, 123.8, 121.6, 60.6, 50.8, 46.5, 41.3, 34.8, 31.6, 25.9, 25.1. HRMS-ESI: C42H62N8NaO3+[M+Na]+ calcd: 749.4838, found: 749.4838.

1,3-bis(4-azidobutyl)-5,5-bis(naphthalen-2-yl)pyrimidine-2,4,6-(1H,3H,5H)-trione-6(iv)

To a stirred solution of 5(iv) (509 mg, 0.75 mmol) in DMF (3 mL) was added NaN$_3$ (146 mg, 2.25 mmol). The reaction was stirred until completion was indicated by TLC (5% EtOAc in CHCl$_3$). Then the reaction mixture was diluted with EtOAc (20 mL) and washed with water (3×20 mL). The organic phase was dried over Na$_2$SO$_4$, filtered and concentrated. The crude product was dissolved in CHCl$_3$ and adsorbed onto celite before purification on silica column using 0-5% EtOAc in CHCl$_3$ to yield 6(iv) (194 mg, 91%).

1H NMR (400 MHz, CDCl$_3$): δ 7.80-7.71 (m, 4H), 7.68 (d, J=8.4 Hz, 2H), 7.57 (s, 2H), 7.51-7.41 (m, 4H), 7.17 (d, J=8.4 Hz, 2H), 3.68 (s, 4H), 3.52 (t, J=7.0 Hz, 4H), 2.85 (t, J=6.6 Hz, 4H), 1.14 (p, J=7.4 Hz, 4H), 1.02 (p, J=7.0 Hz, 4H). 13i) NMR (101 MHz, CDCl$_3$): δ 170.9, 149.6, 133.4, 132.7, 132.5, 128.8, 128.5, 127.8, 127.7, 127.2, 126.6, 126.3, 60.8, 50.7, 45.8, 41.2, 25.8, 24.9. HRMS-ESI: C34H34N8NaO3+[M+Na]+ calcd: 625.2646, found: 625.2647.

1,3-bis(4-azidobutyl)-5,5-bis((4-fluoronaphtalen-1-yl)methyl)pyrimidine-2,4,6-(1H,3H,5H)-trione-6(v)

To a stirred solution of 5(v) (166 mg, 0.23 mmol) in DMF (3 mL) was added NaN$_3$ (45 mg, 0.69 mmol). The reaction was stirred over night until completion was indicated by TLC (CHCl$_3$) Then the reaction mixture was diluted with EtOAc (20 mL) and washed with water (3×30 mL) and brine (30 mL). The organic phase was dried over Na$_2$SO$_4$, filtered and concentrated to yield 6(v) (142 mg, 95%).

1H NMR (400 MHz, CDCl$_3$): δ 8.23 (d, J=8.6 Hz, 2H), 8.08 (d, J=8.3 Hz, 2H), 7.62 (t, J=7.6 Hz, 2H), 7.54 (t, J=7.5 Hz, 2H), 7.22 (t, J=6.6 Hz, 2H), 6.98 (t, J=9.0 Hz, 2H), 4.06 (s, 4H), 3.33 (t, J=6.8 Hz, 4H), 2.94 (t, J=6.4 Hz, 4H), 1.10-0.74 (m, 8H). 13i) NMR (101 MHz, CDCl$_3$): δ 170.9, 158.5 (d, J=253.4 Hz), 149.4, 133.2 (d, J=4.4 Hz), 127.9 (d, J=8.5 Hz), 127.4 (d, J=4.6 Hz), 127.2, 126.4 (d, J=1.9 Hz), 124.8 (d, J=2.6 Hz), 124.1 (d, J=15.7 Hz), 121.1 (d, J=6.1 Hz), 108.8 (d, J=20.0 Hz), 60.0, 50.7, 41.1, 40.7, 25.6, 24.4. HRMS-ESI: C34H32ClF2N8O3−[M+Cl]− calcd: 673.2259, found: 673.2259 4.2.5.

1,3-bis(4-azidobutyl)-5,5-bis(3,5-bis(trifluoromethyl)-benzyl)pyrimidine-2,4,6-(1H,3H,5H)-trione-6(vi)

To a stirred solution of 5(vi) (101 mg, 0.12 mmol) in DMF (1 mL) was added NaN$_3$ (23 mg, 0.35 mmol). The reaction was stirred over night. When full conversion was reached according to MS the reaction mixture was diluted with EtOAc (15 mL) and washed with water (3×20 mL). The organic phase was dried over Na$_2$SO$_4$, filtered and concentrated to yield crude 6(vi) (63 mg, 68%) as white powder.

1H NMR (400 MHz, CDCl$_3$): δ 7.78 (s, 2H), 7.53 (s, 4H), 3.59 (s, 4H), 3.57-3.48 (m, 4H), 3.19 (t, J=6.7 Hz, 4H), 1.42-1.31 (m, 4H), 1.31-1.20 (m, 4H). 13i) NMR (101 MHz, CDCl$_3$): δ 169.6, 148.6, 137.0, 132.3 (q, J=33.6 Hz), 129.9, 123.0 (q, J=272.9 Hz), 122.8-121.9 (m), 59.8, 50.6, 44.5, 41.6, 26.0, 24.9. HRMS-ESI: C30H26(ii) IF12N8O3−[M+Cl]− calcd: 809.1630, found: 809.1622.

1,3-bis(4-aminobutyl)-5,5-bis(4-tertbutylbenzyl)pyrimidin-2,4,6(1H,3H,5H)-trione-7(i)

To a stirred solution of 6(i) (2.16 g, 3.52 mmol) and Et3N (0.98 mL, 7.05 mmol) in i-PrOH:THF (1:1, 10 mL) was added 1,3-propanedithiol (0.1 mL, 0.99 mmol). The mixture was stirred for 5 min before addition of NaBH$_4$ (270 mg, 7.14 mmol). After 72 h reaction time, Boc2O (1.69 g, 7.74 mmol) and K$_2$CO$_3$ (1.94 g, 14.0 mmol) were added and the reaction was stirred for 18 h and evaporated, before EtOAc (20 mL) and water (15 mL) were added and stirred for 30 min. The organic phase was washed with water (3×15 mL) and brine (15 mL) and concentrated. The resulting crude was purified by automated flash chromatography and evaporated. The Boc-protected intermediate was deprotected with TFA (2.2 mL, 28.7 mmol) in CH$_2$Cl$_2$ (10 mL) for 18 h. The reaction mixture was concentrated and the crude product purified by RP automated flash chromatography and lyophilized to yield 7(i) (367 mg, 85%) as the TFA-salt.

1H NMR (400 MHz, CD3OD): δ 7.25 (d, J=7.1 Hz, 4H), 6.98 (d, J=7.2 Hz, 4H), 3.62-3.53 (m, 4H), 3.39 (s, 4H), 2.87 (t, J=7.4 Hz, 4H), 1.55-1.36 (m, 4H), 1.36-1.15 (m, 22H). 13i) NMR (101 MHz, CD3OD): δ 172.3, 163.0 (q, J=34.4 Hz, TFA), 151.9, 151.0, 133.5, 130.3, 126.5, 118.2 (q, J=292.8 Hz, TFA), 61.9, 45.9, 41.7, 40.0, 35.3, 31.7, 25.6, 25.5. HRMS-ESI: C34H51N4O3+[M+H]+ calcd: 563.3956, found: 563.3934.

1,3-bis(4-aminobutyl)-5,5-bis(3,5-dibromobenzyl)methyl)-pyrimidin-2,4,6(1H,3H,5H)-trione-7(ii)

To a stirred solution of 6(ii) (810 mg, 0.99 mmol) and Et3N (0.32 mL, 2.29 mmol) in i-PrOH:THF (1:1, 5 mL) was added 1,3-propanedithiol (0.20 mL, 1.99 mmol). The mixture was stirred for 5 min before addition of NaBH$_4$ (90 mg, 2.37 mmol). After 48 h reaction time, Boc2O (650 mg, 2.97 mmol) were added and the reaction mixture was stirred for 18 h and evaporated. The crude mixture was added EtOAc (15 mL) and water (15 mL) and stirred for 30 min. The organic phase was washed with water (3×15 mL) and brine (15 mL) and concentrated. The resulting crude was purified by automated flash chromatography and evaporated. The Boc-protected intermediate was deprotected with TFA (2 mL, 26 mmol) in CH$_2$Cl$_2$ (5 mL) for 18 h. The reaction mixture was concentrated and the crude product purified by RP automated flash chromatography and lyophilized to yield 7(ii) (374 mg, 38%) as the TFA-salt.

1H NMR (400 MHz, CD3OD): δ 7.66 (s, 2H), 7.23 (s, 4H), 3.68 (t, J=7.7 Hz, 4H), 3.43 (s, 4H), 3.08-2.82 (m, 4H), 1.76-1.48 (m, 4H), 1.49-1.32 (m, 4H). 13i) NMR (101 MHz, CD3OD): δ 171.2, 163.01 (q, J=34.4 Hz, TFA), 150.4, 140.5, 134.5, 132.7, 124.1, 118.24 (q, J=293.3 Hz, TFA). 61.2, 44.8, 42.2, 40.3, 26.3, 25.8. HRMS-ESI: C26H31 79Br4N4O3+[M+H]+ calcd: 762.9124, found: 762.9124.

1,3-bis(4-aminobutyl)-5,5-bis(3,5-di-tert-butylbenzyl)-pyrimidin-2,4,6(1H,3H,5H)-trione-7(iii)

To a stirred solution of 6(iii) (405 mg, 0.55 mol) and Et3N (0.16 mL, 1.15 mmol) in i-PrOH:THF (1:1, 6 mL) was added 1,3-propanedithiol (0.12 mL, 1.15 mmol). The mixture was stirred for 5 min before addition of NaBH$_4$ (44 mg, 1.16 mmol). After 72 h reaction time, Boc2O (490 mg, 2.25 mmol) was added and the reaction was stirred for another night, before diluted with EtOAc (10 mL) and water (10 mL) and stirred for 1 h. The organic phase was washed with water (3×15 mL) and brine (15 mL) and concentrated. The resulting crude was purified by automated flash chromatography and evaporated. The Boc-protected intermediate was deprotected with TFA (1.7 mL, 22.2 mmol) in CH$_2$Cl$_2$ (5 mL) for 6 h. The reaction mixture was concentrated and the crude product purified by RP automated flash chromatography and lyophilized to yield 7(iii) (154 mg, 31%) as the TFA-salt.

1H NMR (400 MHz, CD3OD): δ 7.31 (t, J=1.5 Hz, 2H), 6.89 (d, J=1.6 Hz, 4H), 3.59 (t*, 4H), 3.44 (s, 4H), 2.78 (t*, 4H), 1.40 (p, J=7.7 Hz, 4H), 1.26 (s, 36H), 1.17 (p, J=7.6 Hz, 4H). 13i) NMR (101 MHz, CD3OD): δ 172.3, 162.8 (q, J=34.7 Hz, TFA), 152.3, 151.1, 135.8, 124.7, 122.6, 118.1 (q, J=292.5 Hz, TFA), 61.8, 47.3, 42.0, 39.9, 35.6, 31.9, 25.9, 25.5. *distorted triplets. HRMS-ESI: C42H67N4O3+[M+H]+ calcd: 675.5211, found: 675.5211.

1,3-bis(4-aminobutyl)-5,5-bis(naphtalen-2-yl-methyl)-pyrimidin-2,4,6(1H,3H,5H)-trione-7(iv)

To a stirred solution of 6(iv) (438 mg, 0.73 mmol) and Et3N (0.22 mL, 1.59 mmol) in i-PrOH:THF (1:1, 4 mL) was added 1,3-propanedithiol (0.1 mL, 0.99 mmol). The mixture was stirred for 5 min before addition of NaBH$_4$ (68 mg, 1.81 mmol). After 72 h reaction time, Boc2O (333 mg, 1.53 mmol) and NaHCO$_3$ (244 mg, 2.90 mmol) were added and the reaction was stirred for 18 h, before filtered through a pad of celite and concentrated. The resulting crude was purified by automated flash chromatography and evaporated. The Boc-protected intermediate (305 mg) was deprotected with TFA (2 mL, 26.1 mmol) in CH$_2$Cl$_2$ (5 mL). When MS showed full deprotection, the reaction mixture was concentrated and the crude product purified by RP automated flash chromatography and lyophilized to yield 7(iv) (287 mg, 90%) as the TFA-salt.

1H NMR (400 MHz, CD3OD): δ 7.90-7.68 (m, 6H), 7.60 (s, 2H), 7.52-7.43 (m, 4H), 7.19 (d, J=8.3 Hz, 2H), 3.70 (s, 4H), 3.59-3.50 (m, 4H), 2.56-2.37 (m, 4H), 1.30-0.96 (m, 8H). 13i) NMR (101 MHz, CD3OD): δ 172.2, 162.8 (q, J=35.2 Hz, TFA), 151.0, 134.7, 134.1, 134.0, 129.9, 129.4, 128.8, 128.7, 128.2, 127.6, 127.3, 118.1 (d, J=292.3 Hz, TFA), 62.0, 46.6, 41.7, 39.8, 25.6, 25.5. HRMS-ESI: C34H39N4O3+[M+H]+ calcd: 551.3017, found: 551.3020.

1,3-bis(4-aminobutyl)-5,5-bis((4-fluoronaphtalen-1-yl)methyl)pyrimidin-2,4,6(1H,3H,5H)-trione-7(v)

To a stirred solution of 6(v) (67 mg, 0.105 mmol) and Et3N (0.03 mL, 0.21 mmol) in i-PrOH:THF (1:1, 4 mL) was added 1,3-propanedithiol (0.1 mL, 0.99 mmol). The mixture was stirred for 5 min before addition of NaBH$_4$ (8 mg, 0.21 mmol). After 72 h reaction time, Boc2O (48 mg, 0.22 mmol) and NaHCO$_3$ (35 mg, 0.42 mmol) were added and the reaction was stirred for 18 h, before filtered through a pad of celite and concentrated. The resulting crude was purified by automated flash chromatography and evaporated. The Boc-protected intermediate (72 mg) was deprotected with TFA (0.2 mL, 2.61 mmol) in CH$_2$Cl$_2$ (5 mL). When MS showed full deprotection, the reaction mixture was concentrated and the crude product purified by RP automated flash chromatography and lyophilized to yield 7(v) (82 mg, 89%) as the TFA-salt.

1H NMR (400 MHz, CDCl$_3$): δ 8.34 (d, J=7.9 Hz, 2H), 8.07 (d, J=7.7 Hz, 2H), 7.74-7.53 (m, 4H), 7.38-7.19 (m, 2H), 7.08 (t, J=8.9 Hz, 2H), 4.13 (s, 4H), 3.39-3.33 (m, 4H), 2.60 (t, J=6.8 Hz, 4H), 1.20-1.00 (m, 4H), 0.94-0.71 (m, 4H). 13i) NMR (101 MHz, CDCl$_3$): δ 172.2, 163.11 (q, J=34.1 Hz, TFA), 159.6 (d, J=251.5 Hz), 150.8, 134.5 (d, J=4.4 Hz), 129.3 (d, J=4.5 Hz), 128.4 (d, J=8.5 Hz), 128.2, 127.6 (d, J=1.1 Hz), 126.3 (d, J=2.4 Hz), 125.2 (d, J=15.6 Hz), 121.5 (d, J=6.2 Hz), 118.23 (q, J=292.8 Hz, TFA), 109.76 (d, J=20.2 Hz), 61.0, 41.7, 41.3, 39.9, 25.3, 25.1. HRMS-ESI: C34H37(iv)2N4O3+[M+H]+ calcd: 587.2828, found: 587.2828. 4.2.6.

1,3-bis(4-aminobutyl)-5,5-bis(3,5-bis(trifluoromethyl)-pyrimidin-2,4,6(1H,3H,5H)-trione-7(vi)

To a stirred solution of 6(vi) (63 mg, 0.81 μmol) and Et3N (0.034 mL, 0.24 mmol) in i-PrOH:THF (1:1, 2 mL) was added 1,3-propanedithiol (0.10 mL, 0.99 mmol). The mixture was stirred for 5 min before 12 addition of NaBH$_4$ (92 mg, 0.24 mmol). After 48 h reaction time, Boc2O (70 mg, 0.32 mmol) and K$_2$CO$_3$ (45 mg, 0.33 mmol) were added and the reaction was stirred for another night, before diluted with EtOAc (10 mL) and water (10 mL) and stirred for 1 h. The organic phase was washed with water (3×15 mL) and brine (15 mL) and concentrated. The resulting crude was purified by automated flash chromatography and evaporated. The Boc-protected intermediate was deprotected with TFA (2 mL, 26 mmol) in CH$_2$Cl$_2$ (5 mL) for 18 h. The reaction mixture was concentrated and the crude product purified by RP automated flash chromatography and lyophilized to yield 7(vi) (12 mg, 16%) as the TFA-salt.

1H NMR (400 MHz, CD3OD): δ 7.93 (s, 2H), 7.68 (s, 4H), 3.71 (s, 4H), 3.61-3.54 (m, 4H), 2.87-2.80 (m, 4H), 1.57-1.46 (m, 4H), 1.33-1.22 (m, 4H). 13i) NMR (101 MHz, CD3OD) δ 170.9, 150.1, 139.4, 133.0 (q, J=33.4 Hz, TFA), 131.6-131.1 (m), 124.6 (q, J=272.1 Hz, TFA), 123.0, 61.1, 44.8, 42.3, 40.0, 25.9, 25.7. HRMS-ESI: C30H31F12N4O3+[M+H]+ calcd: 723.2197, found: 723.2161.

1,1'-(4,4'-(5,5-bis(4-tert-butylbenzyl)-2,4,6-trioxodihydropyrimidine-1,3(2H,4H)-diyl)bis(butane-4,1-diyl))diguanidine-8(i)

To a stirred solution of the TFA salt of 7(i) (129 mg, 0.16 mmol) in THF (2 mL) was added NaHCO$_3$ (68 mg, 0.81 mmol) and N,N'-bis-Boc-1-guanylpyrazole (200 mg, 0.64 mmol). The reaction was stirred at r.t. for 48 h. The reaction mixture was concentrated, the crude product was dissolved in EtOAc (20 mL) and washed with 10% citric acid sol. (2×20 mL), 10% NaHCO$_3$ sol. (20 mL) and brine (20 mL). The organic phase was dried over Na$_2$SO$_4$, filtered and concentrated. The crude product was purified by automated flash chromatography and the resulting Boc-protected intermediate was deprotected with TFA (1 mL) in CH$_2$Cl$_2$ for 18 h. The reaction mixture was concentrated and the crude was purified by RP automated flash chromatography and lyophilized to yield 8(i) (16 mg, 11%) as a white powder. 1H NMR (400 MHz, CD3OD): δ 7.24 (d, J=8.3 Hz, 4H), 6.98 (d, J=8.3 Hz, 4H), 3.58 (t, J=6.7 Hz, 4H), 3.39 (s, 4H), 3.13 (t, J=6.6 Hz, 4H), 1.39-1.29 (m, 8H), 1.24 (s, 18H). 13i) NMR (101 MHz, CD3OD) δ 172.4, 162.4 (q, J=35.6 Hz, TFA), 158.7, 151.9, 151.2, 133.4, 130.3, 126.4, 117.9 (q, J=291.5 Hz, TFA), 61.9, 45.9, 42.0, 41.9, 35.3, 31.7, 26.8, 25.8. HRMS-ESI: C36H55N8O3+[M+H]+ calcd: 647.4393, found: 647.4378.

1,1'-(4,4'-(5,5-bis(3,5-dibromobenzyl)-2,4,6-trioxodihydropyrimidine-1,3(2H,4H)-diyl)bis(butane-4,1-diyl))diguanidine-8(ii)

o a stirred solution of the TFA salt of 7(ii) (360 mg, 0.362 mmol) in THF (5 mL) was added NaHCO$_3$ (240 mg, 2.86 mmol) and N,N'-bis-Boc-1-guanylpyrazole (564 mg, 1.82 mmol). When MS showed full guanylation, the reaction mixture was filtered and concentrated. The crude product was dissolved in EtOAc (20 mL) and washed with brine (2×20 mL). The organic phase was dried over Na$_2$SO$_4$, filtered and concentrated. The crude product was purified by automated flash chromatography and the resulting Boc-protected intermediate was deprotected with TFA (0.2 mL) in CH$_2$Cl$_2$ (2 mL) for 18 h. The reaction mixture was concentrated and the crude was purified by RP automated flash chromatography and lyophilized to yield 8(ii) (44 mg, 11%) as a white powder.

1H NMR (400 MHz, CD3OD): δ 7.65 (t, J=1.8 Hz, 2H), 7.22 (d, J=1.7 Hz, 4H), 3.67 (t, J=7.2 Hz, 4H), 3.42 (s, 4H), 3.20 (t, J=6.7 Hz, 4H), 1.52-1.36 (m, 8H). □13i) NMR (101

MHz, CD3OD): δ 171.3, 163.0 (q, J=34.6 Hz, TFA), 158.6, 150.5, 140.5, 134.5, 132.6, 124.1, 118.2 (q, J=292.7 Hz, TFA), 61.2, 44.9, 42.6, 42.1, 27.0, 26.4. HRMS-ESI: C28H35 79Br2 81Br2N8O3+[M+H]+ calcd: 850.9525, found: 850.9532.

1,1'-(4,4'-(5,5-bis(3,5-di-tert-butylbenzyl)-2,4,6-trioxodihydropyrimidine-1,3(2H,4H)-diyl)bis(butane-4,1-diyl))-diguanidine-8(iii)

To a stirred solution of the TFA salt of 7(iii) (118 mg, 0.13 mmol) in THF (3 mL) were added N,N'-bis-Boc-1-guanylpyrazole (245 mg, 0.79 mmol) and NaHCO$_3$ (49 mg, 0.59 mmol) and stirred at r.t. until TLC (CHCl$_3$) showed full conversion. The reaction mixture was diluted with EtOAc (5 mL) and washed with 10% citric acid sol. and brine, dried over Na$_2$SO$_4$, filtered and concentrated. The crude was purified by automated flash chromatography and the resulting Boc-protected intermediate was deprotected with TFA (1.5 mL) in CH$_2$Cl$_2$ (1.5 mL) for 4 h. The reaction mixture was concentrated and the crude was purified by RP automated flash chromatography and lyophilized to yield 8(iii) (44 mg, 34%) as a white powder.

1H NMR (400 MHz, CD3OD): δ 7.30 (t, J=1.8 Hz, 2H), 6.89 (d, J=1.8 Hz, 4H), 3.58* (t, J=7.5 Hz, 4H), 3.44 (s, 4H), 3.06 (t, J=7.0 Hz, 4H), 1.38-1.14 (m, 44H). 13i) NMR (101 MHz, CD3OD): δ 172.4, 162.8 (q, J=35.2 Hz, TFA), 158.6, 152.3, 151.3, 135.8, 124.6, 122.6, 118.0 (q, J=292.3 Hz, TFA), 61.7, 47.3, 42.4, 41.8, 35.6, 31.9, 26.7, 26.2. *distorted triplet. HRMS-ESI: C44H71N8O3+[M+H]+ calcd: 759.5644, found: 759.5637.

1,1'-(4,4'-(5,5-bis(naphthalen-2-ylmethyl)-2,4,6-trioxodihydropyrimidine-1,3(2H,4H)-diyl)bis(butane-4,1-diyl))-diguanidine-8(iv)

To a stirred solution of the TFA salt of 7(iv) (54 mg, 0.069 mmol) in THF (4 mL) were added N,N'-bis-Boc-1-guanylpyrazole (63 mg, 0.20 mmol) and NaHCO$_3$ (41 mg, 0.48 mmol) and stirred at r.t. until TLC (CHCl$_3$) showed full conversion. The reaction mixture was diluted with EtOAc (5 mL) and washed with 10% citric acid sol. (2×10 mL), and brine (10 mL), dried over Na$_2$SO$_4$, filtered and concentrated. The Boc-protected intermediate was dissolved in CHCl$_3$ and adsorbed onto Celite before purification on a silica column using CHCl$_3$ as mobile phase. The Boc-protected intermediate (64 mg of a total of 104 mg, 0.057 mmol) was deprotected with TFA (0.2 mL) in CH$_2$Cl$_2$ (4 mL) until TLC showed full conversion. The reaction mixture was concentrated and purified by RP automated flash chromatography and lyophilized to yield 8(iv) (60 mg, 99%) as a white powder.

1H NMR (400 MHz, CD3OD): δ 7.85-7.69 (m, 6H), 7.59 (s, 2H), 7.53-7.40 (m, 4H), 7.20 (dd, J=8.4, 1.8 Hz, 2H), 3.69 (s, 4H), 3.54 (t, J=7.1 Hz, 4H), 2.80 (t, J=7.1 Hz, 4H), 1.21-1.08 (m, 4H), 1.08-0.98 (m, 4H). □ 13i) NMR (101 MHz, CD3OD): δ 172.3, 163.1 (q, J=34.3 Hz, TFA), 158.5, 151.0, 134.7, 134.1, 134.0, 129.8, 129.4, 128.7, 128.6, 128.3, 127.6, 127.3, 118.2 (q, J=293.0 Hz, TFA), 62.0, 46.6, 42.1, 41.8, 26.6, 25.9. HRMS-ESI: C36H43N8O$_3$+[M+H]+ calcd: 635.3450, found: 635.3448.

1,1'-(4,4'-(5,5-bis((4-fluoronaphthalen-1-yl)methyl)-2,4,6-trioxodihydropyrimidine-1,3(2H,4H)-diyl)bis(butane-4,1-diyl))diguanidine-8(v)

To a stirred solution of the TFA salt of 7(v) (35 mg, 43 µmol) in THF (3 mL) were added N,N'-bis-Boc-1-guanylpyrazole (38 mg, 122 µmol) and NaHCO$_3$ (25 mg, 0.29 mmol) and stirred at r.t. until TLC (CHCl$_3$) showed full conversion. The reaction mixture was diluted with EtOAc (5 mL) and washed with 10% citric acid sol. and brine, dried over Na$_2$SO$_4$, filtered and concentrated. The Boc-protected intermediate was dissolved in CHCl$_3$ and adsorbed onto Celite before purification on a silica column using CHCl$_3$ as mobile phase. The Boc-protected intermediate (41 mg of a total of 95 mg, 0.038 mmol) was deprotected with TFA (0.1 mL) in CH$_2$Cl$_2$ (4 mL) until TLC showed full conversion. The reaction mixture was concentrated and purified by RP automated flash chromatography and lyophilized to yield 8(v) (20 mg, 52%) as a white powder.

1H NMR (400 MHz, CD3OD): δ 8.32 (d, J=8.6 Hz, 2H), 8.06 (d, J=7.9 Hz, 2H), 7.71-7.55 (m, 4H), 7.25 (dd, J=8.0, 5.5 Hz, 2H), 7.06 (dd, J=10.2, 8.1 Hz, 2H), 4.12 (s, 4H), 3.35 (t, J=7.2 Hz, 4H), 2.87 (t, J=7.1 Hz, 4H), 1.00 (p, J=7.2 Hz, 4H), 0.86 (p, J=7.4, 6.8 Hz, 4H). 13i) NMR (101 MHz, CD3OD): δ 172.2, 163.1 (q, J=34.1 Hz, TFA), 159.6 (d, J=251.6 Hz), 158.5, 150.9, 134.5 (d, J=4.3 Hz), 129.2 (d, J=4.6 Hz), 128.9 (d, J=8.5 Hz), 128.2, 127.6 (d, J=1.6 Hz), 126.2 (d, J=2.5 Hz), 125.2 (d, J=15.8 Hz), 121.5 (d, J=6.2 Hz), 118.2 (q, J=292.8 Hz, TFA), 109.7 (d, J=20.2 Hz), 60.9, 42.1, 41.8, 41.4, 26.5, 25.4. HRMS-ESI: C36H41F2N8O3+[M+H]+ calcd: 671.3264, found: 671.3244.

Biological Test Methods

Minimum Inhibitory Concentration (MIC) Assay

Working solutions of the test derivatives were prepared with up to 100% DMSO and stored at −20° C. If necessary, the solutions were heated to 40-80° C. before testing to facilitate complete dissolution. Double-distilled water was used in all dilutions prepared. The final concentration of DMSO in the test series was ≤1% and did not affect the assay results. A microdilution susceptibility test was used for MIC determination according to Clinical and Laboratory Standards Institute, "Methods for Dilution Antimicrobial Sisceptibility Tests for Bacteria That Graw Aerobically", Approved Standard M07-A9, edition 2012, with modifications as described by Igumnova et al (Bioorg Med Chem, 2016, 24 (22), 5884-5894).

Briefly, the bacterial inoculum was adjusted to approximately 2.5-3×10$^4$ cells/mL in Mueller-Hinton broth (MHB, Difco Laboratories, USA), and incubated in a ratio of 1:1 with test derivatives in polystyrene 96-well flat-bottom microplates (NUNC, Roskilde, Denmark). Positive growth control (without test derivatives) and negative control (without bacteria) were included. The reference antibiotic was oxytetracycline hydrochloride (Sigma Aldrich, Saint Louis, Mo., USA). The microplates were incubated in an EnVision microplate reader (Perkin-Elmer, Turku, Finland) placed in an incubator set to 35° C. for 48 h. The MIC value was defined as the lowest concentration of derivative resulting in no bacterial growth as determined by OD$_{600}$ measurement. All derivatives were tested in three parallels.

Antimicrobial Screening Against Clinical Isolates

The MIC was determined as explained above with some exceptions; working solutions of test derivatives were prepared from concentrated DMSO stocks stored at room temperature, the density of the bacterial inoculum was increased 40× to 1-1.2×10$^6$ cells/mL, enterococci were incubated in Brain Heart Infusion broth (BHIB, Difco Laboratories, USA), the microplates were incubated for 24 h, and the derivatives were tested in four parallels.

Determination of Haemolytic Activity

Hemolysis was determined using a heparinized fraction (1000 IU/mL) of freshly drawn blood. Blood collected in EDTA containing test tubes (Vacutest®, KIMA, Arzergrande, Italy) was used for determination of the hematocrit (hct). The heparinized blood was washed 3× with pre-warmed PBS and adjusted to a final hct of 4%. Derivatives in DMSO (50 mM) were added to a 96-well polypropylene V-bottom plate (NUNC, Fisher Scientific, Oslo, Norway) and serially diluted. The test concentration range was 500-4 µM with DMSO contents ≤1%. A solution of 1% triton X-100 was used as positive control for 100% hemolysis. As negative control a solution of 1% DMSO in PBS buffer was included. No signs of DMSO toxicity were detected. RBCs (1% v/v final concentration) were added to the well plate and incubated at 37° C. and 800 rpm for 1 h. After centrifugation (5 min, 3000 g), 100 µL of each well were transferred to a 96-well flat bottom plate and absorbance was measured at 545 nm with a microplate reader (VersaMax™, Molecular Devices, Sunnyvale, Calif., USA). The percentage of hemolysis was calculated as the ratio of the absorbance in the derivative-treated and surfactant treated samples, corrected for the PBS background. Three independent experiments were performed and $EC_{50}$ values are presented as averages.

Example 2

Further compounds of interest according to the invention are set out in FIG. 4.

Example 3-Anti-Biofilm Activity

*S. epidermidis* was used to assess the effects of the test compounds on inhibiting biofilm formation. Tryptic soy broth (TS; Merck, Darmstadt, Germany) was used as growth media.

A culture of *S. epidermidis* grown overnight in TS was diluted with fresh TS containing 1% glucose (1:100). 50 µL aliquots were transferred to a 96-well microtiter plate, and 50 µL of the test compounds dissolved in water at different concentrations was added. After incubation at 37° C. overnight, the bacterial suspension was discarded carefully before the wells were washed with water. The plate was dried and the biofilm fixed by incubation for 1 hour at 55° C. before the cells attached to the surface were stained with 0.1% crystal violet (100 µL) for 5 minutes. The crystal violet solution was removed and the plate once more washed with water and dried at 55° C. for 1 hour. After adding 70 µL of 70% ethanol, the plate was incubated at room temperature for 10 minutes.

Biofilm formation was observed by visually inspecting the plates. The MIC was defined as the lowest concentration where no biofilm formation was visible.

An *S. epidermidis* suspension, diluted with 50 µL of water, was used as a positive control, and 50 µL *Staphylococcus haemolyticus* suspension with 50 µL of water was used as a negative control. A mixture of 50 µL water and 50 µL TS was used as assay control.

| Compound | Anti-biofilm $IC_{50}$ (µg/ml) |
|---|---|
| 7(i) | 4 |
| 7(ii) | 6 |
| 7(iii) | 1 |
| 7(iv) | 4 |
| 7(v) | 4 |
| 8(i) | 1 |
| 8(ii) | 1 |
| 8(iii) | 2 |

| Compound | Anti-biofilm $IC_{50}$ (µg/ml) |
|---|---|
| 8(iv) | 1 |
| 8(v) | 1 |

Example 4—Anti-Cancer Activity Against A2058 Cells

Cytotoxicity of the test compounds was evaluated after 72 hour exposure to human Caucasian metastatic melanoma (A2058, ATCC CRL-11147) cells.

A2058 cells were grown overnight (2,000 cells/well), and then incubated with the test compounds (range of concentrations) diluted in MEM Earle's supplemented with gentamycin (10 µg/mL), non-essential amino acids (1%), sodium pyruvate (1 mM), L-alanyl-Lglutamine (2 mM), but without FBS (total volume was 100 µl) for 24 hours. Ten µL of CellTiter 96® AQueous One Solution Reagent (Promega, Madison, Wis., USA) was added, and the plates were then further incubated for 1 hour.

Absorbance was measured at 485 nm in a DTX 880 Multimode Detector. Results were calculated as % survival compared to negative (assay media) and positive (Triton X-100; Sigma-Aldrich) controls.

| Compound | Anti-cancer $IC_{50}$ (µg/ml) |
|---|---|
| 7(i) | 1 |
| 7(ii) | 1 |
| 7(iii) | 1 |
| 7(iv) | 1 |
| 7(v) | 1 |
| 8(i) | 2 |
| 8(ii) | 2 |
| 8(iii) | 33 |
| 8(iv) | 8 |
| 8(v) | 8 |

Compound 9 (below) was also tested, and found to have an $IC_{50}$ value of 2.9 µg/ml.

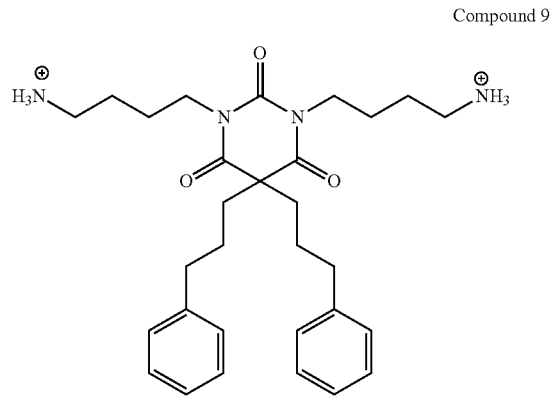 [SMILES: [NH3+]CCCCN1C(=O)N(CCCC[NH3+])C(=O)C(CCCc2ccccc2)(CCCc2ccccc2)C1=O]

Compound 9

Example 4

Methods of the synthesis of hydantoins following the "Bucherer-Bergs reaction for hydantoin synthesis" are well known in the art (e.g. Bucherer, H. T.; Brandt, W. J. Prakt. Chem. 1934, 140, 129; Bucherer, H. T.; Steiner, W. J. Prakt. Chem. 1934, 140, 291; and Bucherer, H. T.; Lieb, V. A. J. Prakt. Chem. 1934, 141, 5).

This method, which is shown below, could be used for the synthesis of compounds of Formula (III). Specifically, as shown in scheme 2 below, the precursor hydantoins could be prepared by reacting the appropriate substituted carbonyl compounds with potassium cyanide (KCN) and ammonium carbonate [(NH4)2CO3], or from cyanohydrin and ammonium carbonate in a multiple component reaction.

Scheme 2

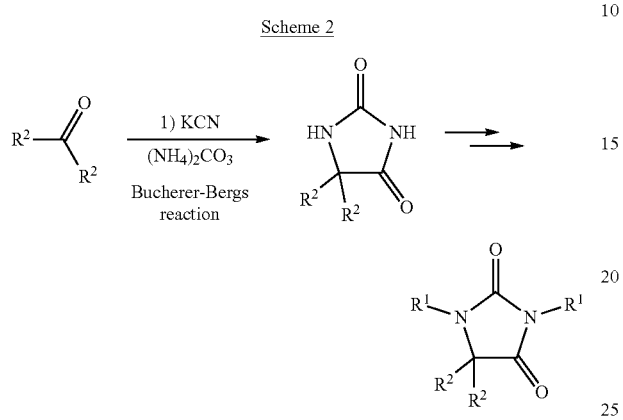

For introducing the cationic $R_1$ groups, the same methods discussed above for the synthesis of compounds 7(i)-8(v) (i.e. compounds of Formula (II)) could be used. One possible synthesis is shown in scheme 3 below.

Scheme 3

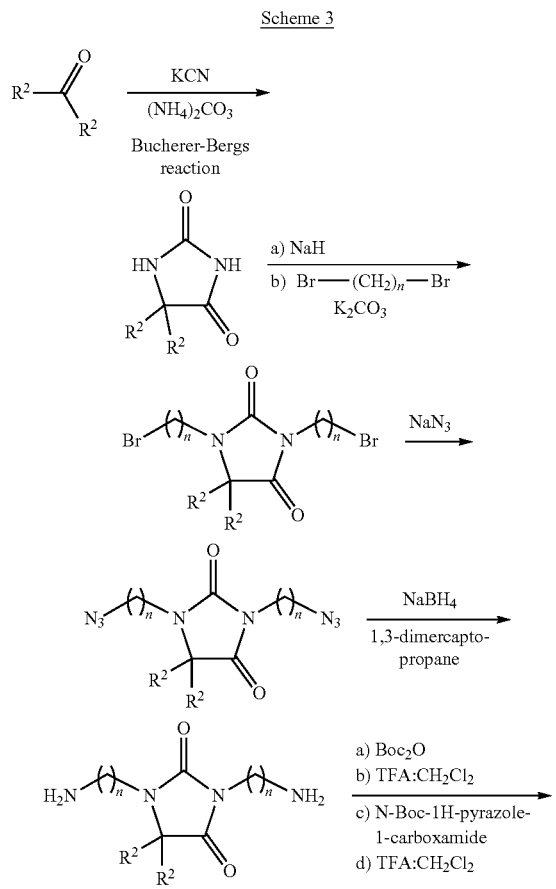

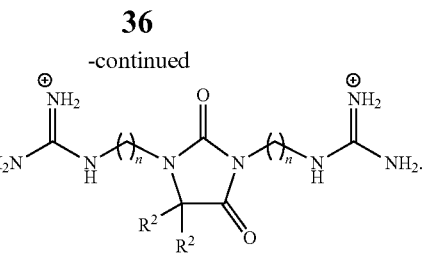

The invention claimed is:

1. A compound of Formula (I)

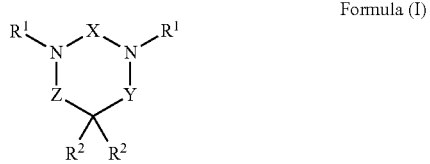

or a stereoisomer, a tautomer, or a solvate thereof, wherein:
X is $CH_2$ or C=W;
Y is $CH_2$ or C=W;
Z is a bond, $CH_2$ or C=W;
W is N, O or S;
each $R^1$, which may be the same or different, comprises 2-15 non-hydrogen atoms and at least one cationic group which has a net charge of at least +1 at pH 7;
each $R^2$, which may be the same or different, is lipophilic and comprises at least 7 non-hydrogen and non-fluorine atoms;
alternatively the $R^2$ groups are linked or fused to form a lipophilic group having a total of at least 14 non-hydrogen and non-fluorine atoms, or at least 12 non-hydrogen and non-fluorine atoms when cyclic groups within each group are fused together;
at least one $R^2$ group contains a cyclic group; and
the compound has a net positive charge of at least +2 at pH 7.

2. The compound of claim 1, wherein W is O.

3. The compound of claim 1, wherein X is C=W and Y is C=W and Z is a bond or C=W.

4. The compound of claim 3, wherein Z is a bond.

5. The compound of claim 3, wherein Z is C=W.

6. The compound of claim 1, wherein the compound is a compound of Formula (II)

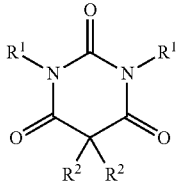

wherein $R^1$ and $R^2$ are as defined in claim 1.

7. The compound of claim 1, wherein $R^1$ comprises a cationic amine group or a cationic imine group.

8. The compound of claim 1, wherein $R^1$ comprises at least one of $-NR_{3+}$, $=NR_{2+}$, $-NR_{2+}-$, and $=NR^+-$, wherein each R is the same or different at each occurrence and is H or alkyl.

9. The compound of claim 8, wherein $R^1$ comprises —$NR_{3+}$ or —NR—C(=$NR_{2+}$)—$NR_2$ as the cationic group, wherein R is the same or different and is H or alkyl.

10. The compound of claim 8, wherein R is H, $CH_3$ or $CH_2CH_3$.

11. The compound of claim 1, wherein the $R^2$ groups are not linked or fused together.

12. The compound of claim 11, wherein each $R^2$ group comprises at least 8 non-hydrogen and non-fluorine atoms.

13. The compound of claim 12, wherein each $R^2$ group comprises at least 9 non-hydrogen and non-fluorine atoms.

14. The compound of claim 1, wherein both $R^2$ groups contain a cyclic group.

15. A formulation comprising a compound of Formula (I) as defined in claim 1 in admixture with a suitable diluent, carrier or excipient.

16. A method of treating a microbial infection, comprising administering to a patient in need thereof a therapeutically effective amount of a compound of Formula (I) as defined in claim 1.

17. The method of claim 16, wherein the microbial infection is bacterial or fungal infection.

18. A method of treating cancer, comprising administering to a patient in need thereof a therapeutically effective amount of a compound of Formula (I) as defined in claim 1.

19. The compound of claim 1, wherein $R^1$ is

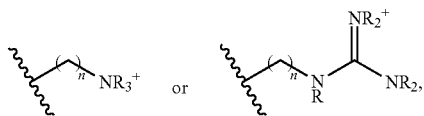

wherein each R independently is H or alkyl, and n is 1-10.

20. The compound of claim 19, wherein $R^1$ is

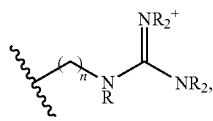

wherein R is H, $CH_3$ or $CH_2CH_3$ and n is 2-8.

21. The compound of claim 19, wherein each $R^2$ group is selected from alkyl, alkenyl, alkynyl, heteroalkyl, alkoxy, haloalkoxy, aryl, heteroaryl, cycloalkyl, or heterocycloalkyl, each of which may optionally be substituted with a substituent selected from the group consisting of halo, —CN, —$R^4NO_2$, —$R^4OR^3$, —$R^4$(=O)$R^3$, —$R^4OC$(=O)$R^3$, —$R^4O_2R^3$, —$R^4N(R^3)_2$, —$R^4$(=O)N($R^3$)$_2$, —$R^4OC$(=O)N($R^3$)$_2$, —$R^4NR^3$(=O)$R^3$, —$R^4NR^3$(=O)O$R^3$, alkyl, alkenyl, alkynyl, haloalkyl, alkoxy, haloalkoxy, aryl, heteroaryl, cycloalkyl, and heterocycloalkyl;
wherein
$R^4$ is a bond or alkyl;
$R^3$ is selected from the group consisting of H, alkyl, alkenyl, alkynyl, heteroalkyl, alkoxy, haloalkoxy, aryl, heteroaryl, cycloalkyl, and heterocycloalkyl.

22. The compound of claim 19, wherein $R^2$ is optionally substituted phenyl, naphthyl or pyridine.

23. The compound of claim 19, wherein each $R^2$ group is -L-$R_x$, wherein:
L is a bond, alkyl, alkenyl, alkynyl, heteroalkyl, alkoxy or haloalkoxy; and
$R_x$ is aryl, heteroaryl, cycloalkyl, or heterocycloalkyl group, optionally substituted with a substituent selected from the group consisting of halo, —CN, —$R^4NO_2$, —$R^4OR^3$, —$R^4$(=O)$R^3$, —$R^4OC$(=O)$R^3$, —$R^4O_2R^3$, —$R^4N(R^3)_2$, —$R^4$(=O)N($R^3$)$_2$, —$R^4OC$(=O)N($R^3$)$_2$, —$R^4NR^3$(=O)$R^3$, —$R^4NR^3$(=O)O$R^3$, alkyl, alkenyl, alkynyl, haloalkyl, alkoxy, haloalkoxy, aryl, heteroaryl, cycloalkyl, and heterocycloalkyl;
wherein
$R^4$ is a bond or alkyl;
$R^3$ is selected from the group consisting of H, alkyl, alkenyl, alkynyl, heteroalkyl, alkoxy, haloalkoxy, aryl, heteroaryl, cycloalkyl, and heterocycloalkyl.

24. The compound of claim 23, wherein L is $C_{1-3}$ alkyl, $R_x$ is an optionally substituted group selected from the group consisting of phenyl, naphthyl and pyridine.

25. The compound of claim 21, wherein the compound is

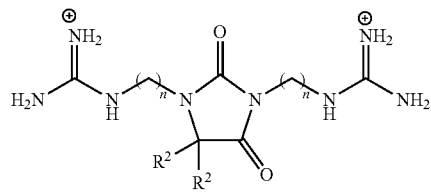

wherein n is 1-10.

26. The compound of claim 1, which is selected from the group consisting of

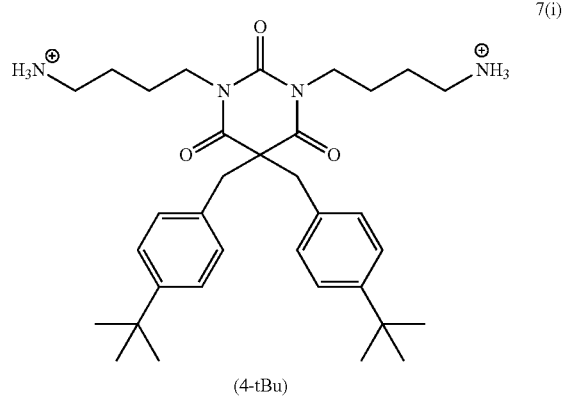

(4-tBu)

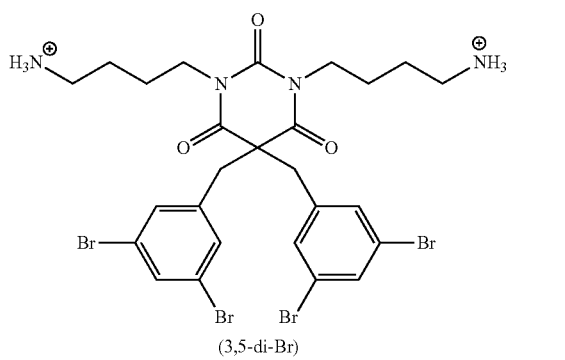

(3,5-di-Br)

-continued
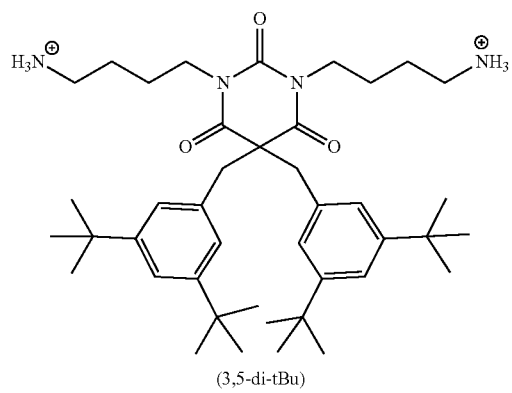
7(iii)
(3,5-di-tBu)
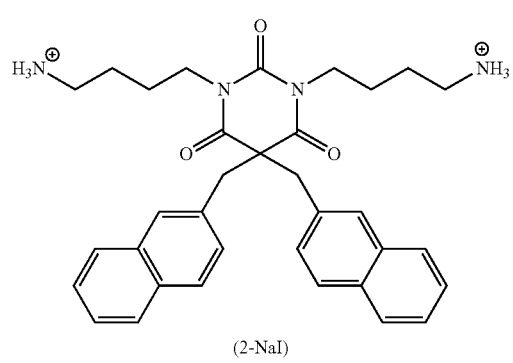
7(iv)
(2-Nal)
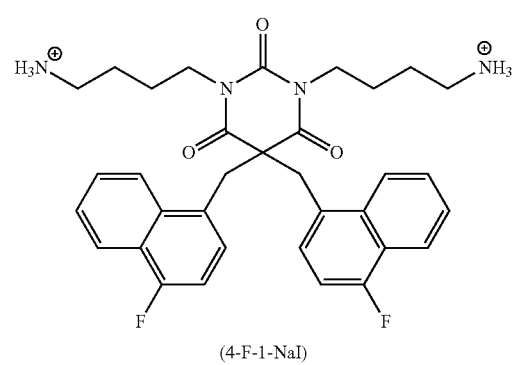
7(v)
(4-F-1-Nal)
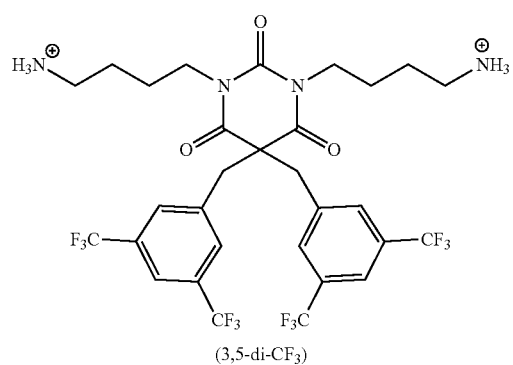
7(vi)
(3,5-di-CF3)
-continued
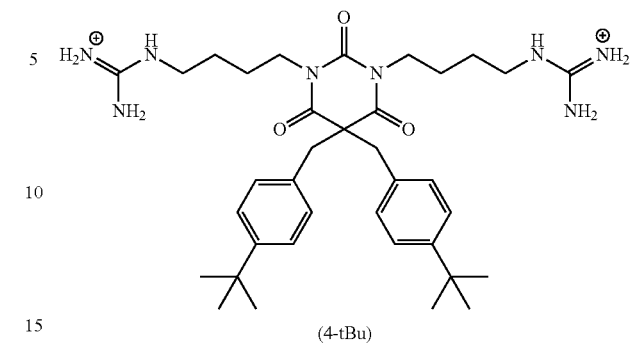
8(i)
(4-tBu)
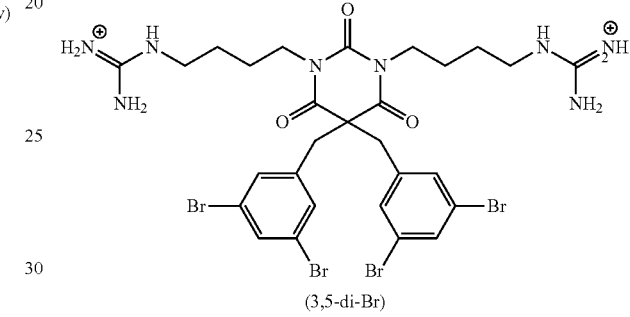
8(ii)
(3,5-di-Br)
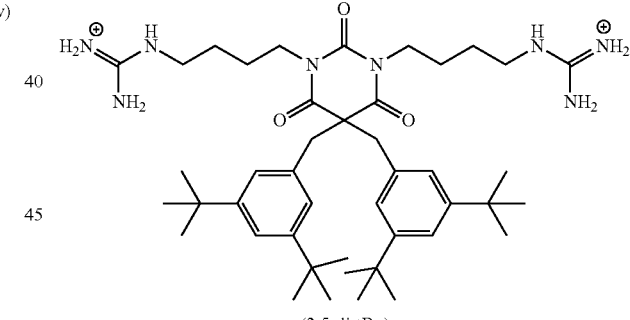
8(iii)
(3,5-di-tBu)
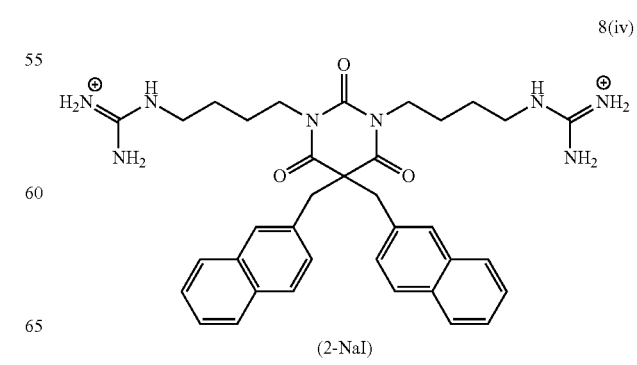
8(iv)
(2-Nal)

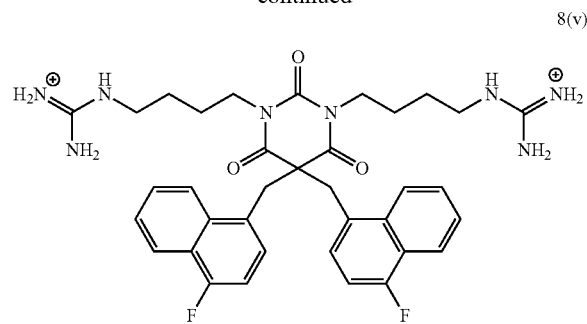
27. The compound of claim 19, which is
28. The compound of claim 1, wherein the cationic group is a cationic amine or a cationic imine.
* * * * *